US009694068B2

(12) United States Patent
Golovkin

(10) Patent No.: US 9,694,068 B2
(45) Date of Patent: Jul. 4, 2017

(54) METHODS AND COMPOSITIONS TO PRODUCE VACCINES AGAINST SMALLPOX IN PLANTS

(71) Applicant: Maxim Golovkin, Huntingdon Valley, PA (US)

(72) Inventor: Maxim Golovkin, Huntingdon Valley, PA (US)

(73) Assignee: PHARMA GREEN LLC, Feasterville-Trevose, PA (US)

( * ) Notice: Subject to any disclaimer, the term of this patent is extended or adjusted under 35 U.S.C. 154(b) by 1035 days.

(21) Appl. No.: 13/849,154

(22) Filed: Mar. 22, 2013

(65) Prior Publication Data

US 2013/0266608 A1 Oct. 10, 2013

Related U.S. Application Data

(60) Provisional application No. 61/614,167, filed on Mar. 22, 2012.

(51) Int. Cl.

| | | |
|---|---|---|
| C12N 15/62 | (2006.01) | |
| C12N 15/39 | (2006.01) | |
| C12N 15/82 | (2006.01) | |
| C07K 14/07 | (2006.01) | |
| A61K 39/275 | (2006.01) | |
| A61K 39/12 | (2006.01) | |
| A61K 39/00 | (2006.01) | |

(52) U.S. Cl.
CPC .......... *A61K 39/275* (2013.01); *A61K 39/12* (2013.01); *C12N 15/8258* (2013.01); *A61K 2039/543* (2013.01); *A61K 2039/545* (2013.01); *A61K 2039/55505* (2013.01); *A61K 2039/55544* (2013.01); *A61K 2039/55561* (2013.01); *C12N 2710/24134* (2013.01)

(58) Field of Classification Search
None
See application file for complete search history.

(56) References Cited

U.S. PATENT DOCUMENTS

| | | | |
|---|---|---|---|
| 5,316,931 A | 5/1994 | Donson et al. | |
| 5,589,367 A | 12/1996 | Donson et al. | |
| 5,889,190 A | 3/1999 | Donson et al. | |
| 5,889,191 A | 3/1999 | Turpen | |
| 7,667,092 B2 | 2/2010 | Klimyuk et al. | |
| 7,670,801 B2 | 3/2010 | Gleba et al. | |
| 7,763,458 B2 | 7/2010 | Gleba et al. | |
| 8,003,609 B2 | 8/2011 | Klimyuk et al. | |
| 8,093,458 B2 | 1/2012 | Marillonnet et al. | |
| 8,148,609 B2 | 4/2012 | Koprowski et al. | |
| 2003/0101477 A1* | 5/2003 | Colliver | C12N 9/0004 800/278 |
| 2005/0059053 A1* | 3/2005 | Fischer | C07H 21/04 435/6.14 |
| 2007/0136890 A1* | 6/2007 | Allison | C12N 15/8239 800/280 |

OTHER PUBLICATIONS

Golovkin et al (PNAS, 2007, 104(16): 6864-6869; cited on IDS).*
Sakhatskyy et al (Virology, 2008, 371:98-107).*
Giritch et al (PNAS, 2006, 103(40): 14701-14706; cited on IDS).*
Christensen et al (The Plant Cell, 2005, 17(10): 2805-2816).*
Palme et al (The Plant Cell, 1992, 4: 193-201).*
GenBank S31584 (published 2004).*
GenBank ABO09596 (published 2009).*
Marillonnet Sylvestre, et al., In planta engineering of viral RNA replicons: Efficient assembly by recombination of DNA modules delivered by Agrobacterium, Proc Natl Acad Sci USA, 2004, 101 (18): 6852-6857.
Marillonnet Sylvestre, et al., "Systemic Agrobacterium tumefaciens—mediated transfection of viral replicons for efficient transient expression in plants," Nature Biotechnology, 2005, 23: 718-723.
Y. Gleba, et al., "Magnifection—a new platform for expressing recombinant vaccines in plants," Vaccine, 2005, 23: 2042-2048.
Kurt D. Reed, et al., "The Detection of Monkeypox in Humans in the Western Hemisphere," The New England Journal of Medicine, 2004, 350: 342-350.
Aysegul Nalca, et al., "Reemergence of monkeypox: Prevalence, diagnostics, and countermeasures," Clinical Infectious Diseases, 2005, 41:1765-1771.
Donald A. Henderson, "The Looming Threat of Bioterrorism," Science, 1999, 283: 1279-1282.
Martin Enserink, "Biodefense—Smallpox vaccines: Looking beyond the next generation," Science, 2004, 304: 809.
Frank Fenner, et al., "Smallpox and its Eradication," History of International Public Health, 1988, No. 6, World Health Organization, Geneva.
Erika Hammarlund, et al., "Multiple diagnostic techniques identify previously vaccinated individuals with protective immunity against monkeypox," Nature Medicine 2005, 11 (9): 1005-1008.
Vincent A. Fulginiti, et al., "Smallpox vaccination: A review, part I. Background, vaccination technique, normal vaccination and revaccination, and expected normal reactions," Clinical Infectious Diseases, 2003, 37:241-250.
Aklile Berhanu, et al., "Vaccination of BALB/c mice with *Escherichia coli*-expressed vaccinia virus proteins A27L, pB5R, and D8L protects mice from lethal vaccinia virus challenge," Journal of Virology, 2008, 82:3517-29.
J.W. Hooper, et al., "DNA vaccination with vaccinia virus pL1R and pA33R genes protects mice against a lethal poxvirus challenge," Virology, 2000, 266: 329-339.

(Continued)

*Primary Examiner* — John S Brusca
*Assistant Examiner* — Stephen Uyeno
(74) *Attorney, Agent, or Firm* — Volpe and Koenig, P.C.

(57) ABSTRACT

Compositions and methods for producing plant-derived immunogenic compositions that confer immunity against smallpox in a subject are provided. Plants engineered to produce antigenic proteins as well as expression cassettes comprising nucleic acids encoding proteins thereof are described. Methods of immunizing subjects with plant-derived compositions are also provided.

9 Claims, 16 Drawing Sheets

(56) References Cited

OTHER PUBLICATIONS

J.W. Hooper, et al., "Four-gene-combination DNA vaccine protects mice against a lethal vaccinia virus challenge and elicits appropriate antibody responses in nonhuman primates," Virology, 2003, 306:181-195.

J.W. Hooper, et al., "Smallpox DNA Vaccine Protects Nonhuman Primates against Lethal Monkeypox," Journal of Virology, 2004, 78:4433-4443.

Christiana Fogg, et al., "Protective Immunity to Vaccinia Virus Induced by Vaccination with Multiple Recombinant Outer Membrane Proteins of Intracellular and Extracellular Virions," Journal of Virology, 2004, 78: 10230-10237.

Jean-Michel Heraud, et al., "Subunit Recombinant Vaccine Protects against Monkeypox," The Journal of Immunology, 2006, 177: 2552-2564.

Min Fang, et al., "Immunization with a single extracellular enveloped virus protein produced in bacteria provides partial protection from a lethal orthopoxvirus infection in a natural host," Virology, 2006, 345:231-243.

Christiana N. Fogg, et al., "Adjuvant-enhanced antibody responses to recombinant proteins correlates with protection of mice and monkeys to orthopoxvirus challenges," Vaccine, 2007, 25(15):2787-2799.

Edward P. Rybicki, "Plant-produced vaccines: promise and reality," Drug Discovery Today, 2009, 14 (1/2):16-24.

Jeffrey L. Fox, "Turning plants into protein factories," Nature Biotechnology, 2006, 24 (10):1191-1193.

Julian K-C. Ma, et al., "Plant-derived pharmaceuticals—the road forward," Trends in Plant Science, 2005, 10:580-585.

Robert Boehm, "Bioproduction of therapeutic proteins in the 21st century and the role of plants and plant cells as production platforms," Annals of the New York Academy of Sciences, 2007, 1102:121-134.

Hilary Koprowski, "Vaccines and sera through plant biotechnology," Vaccine, 2005, 23: 1757-1763.

David Lienard, et al., "Pharming and transgenic plants," Biotechnology Annual Review, 2007, 13:115-147.

Anna Modelska, et al., "Immunization against rabies with plant-derived antigen," Proc Natl Acad Sci U S A, 1998, 95(5)2481-2485.

Natalia Pogrebnyak, et al., "Collard and cauliflower as a base for production of recombinant antigens," Plant Science, 2006, 171: 677-685.

Natalia Pogrebnyak, et al., "Severe acute respiratory syndrome (SARS) S protein production in plants: Development of recombinant vaccine," Proc Natl Acad Sci USA, 2005, 102: 9062-9067.

Robert Brodzik, et al., "Plant-derived EpCAM antigen induces protective anti-cancer response," Cancer Immunology, Immunotherapy, 2008, 57: 317-323.

J. Kapusta, et al., "A plant-derived edible vaccine against hepatitis B ," The FASEB Journal, 1999, 13:1796-1799.

Kisung Ko, et al., "Inhibition of tumor growth by plant-derived mAb," Proc Natl Acad Sci U S A, 2005, 102 (19):7026-7030.

S. Spitsin, et al., "Immunological assessment of plant-derived avian flu H5/HA1 variants," Vaccine, 2009, 27:1289-1292.

Carla Portocarrero, et al., "Immunogenic properties of plant-derived recombinant smallpox vaccine candidate ppB5," Vaccine, 2008, 26: 5535-5540.

Maxim Golovkin, et al., "Smallpox subunit vaccine produced in Planta confers protection in mice," Proc Natl Acad Sci U S A, 2007, 104(16):6864-6869.

Nicholas J. Mantis, et al., "Immunization of mice with recombinant gp41 in a systemic prime/mucosal boostprotocol induces HIV-1-specific serum IgG and secretory IgA antibodies," Vaccine, 2001, 19:3990-4001.

Andreas Brave, et al., "Intranasal immunization of young mice with a multigene HIV-1 vaccine in combination with the N3 adjuvant induces mucosal and systemic immune responses," Vaccine, 2008, 26(40):5075-5078.

M. Haile, et al., "Immunization with heat-killed Mycobacterium bovis bacille Calmette-Guerin (BCG) in Eurocine L3 adjuvant protects against tuberculosis," Vaccine, 2004, 22(11-12):1498-1508.

Ulf Schroder, et al., "Nasal and parenteral immunizations with diphtheria toxoid using monoglyceride/fatty acid lipid suspensions as adjuvants," Vaccine, 1999, 17(15-16):2096-2103.

Anna U. Bielinska, et al., "A novel, killed-virus nasal vaccinia virus vaccine," Clinical and Vaccine Immunology, 2008, 15(2):348-358.

Stuart N. Isaacs, et al., "Characterization of a vaccinia virus-encoded 42-kilodalton class I membrane glycoprotein component of the extracellular virus envelope," Journal of Virology, 1992, 66: 7217-7224.

Mansun Law, et al., "Antibody neutralization of the extracellular enveloped form of vaccinia virus," Virology, 2001, 280:132-142.

Lydia Aldaz-Carol, et al., "Epitope-Mapping Studies Define Two Major Neutralization Sites on the Vaccinia Virus Extracellular Enveloped Virus Glycoprotein pB5R," Journal of Virology, 2005, 79: 6260-6271.

Yuhong Xiao, et al., "A protein based smallpox vaccine protects mice from vaccinia and ectromelia virus challenges when given as a prime and single boost," Vaccine, 2006, 25, 1214-1224.

Manmohan Singh, Derek T. O'Hagan, "Recent advances in vaccine adjuvants," Pharmaceutical Research, 2002 19:715-728.

Anatoly Giritch, et al., "Rapid high-yield expression of full-size IgG antibodies in plants coinfected with noncompeting viral vectors," Proc Natl Acad Sci U S A, 2006, 103:14701-14706.

Andrew Hiatt, Michael Pauly, "Monoclonal antibodies from plants: a new speed record," Proc Natl Acad Sci U S A, 2006, 103:14645-14646.

Matthias Schahs, et al., "Production of a monoclonal antibody in plants with a humanized N-glycosylation pattern," Plant Biotechnology Journal, 2007, 5:657-663.

Richard Strasser, et al., "Generation of glyco-engineered Nicotiana benthamiana for the production of monoclonal antibodies with a homogeneous human-like N-glycan," Plant Biotechnology Journal, 2008, 6:392-402.

Rodolfo Valdez, et al., "Comparison of different ligand densities in immunoaffinity chromatography of the plantibody HB-01 coupled to Sepharose CL-4B topurify the rHBsAg," Journal of Chromatography B, 2007, 852 (1-2): 1-7.

Maxim Golovkin, "Production of Recombinant Pharmaceuticals Using Plant Biotechnology," Chapter 14, In: Bioprocess Sciences and Technology, 2011, Nova Sciences Publishers.

Maxim Golovkin, "Plant biotechnology for production of recombinant pharmaceuticals," Human Vaccines, 2011, 7 (3): 303-304.

Keiichi Itakura, et al., "Expression in *Escherichia coli* of a Chemically Synthesized Gene for the Hormone Somatostatin," Science 1977, 198:1056-1063.

Jeffrey L. Bennetzen and Benjamin D. Hall, "Codon Selection in Yeast," The Journal of Molecular Chemistry, 1982, 257: 3026-3031.

Yasukazu Nakamura, et al., "Codon Usage Tabulated from International DNA Sequence Databases: Status for the Year 2000 ," Nucleic Acid Research, 2000, 28:292.

Els N. Meeusen, "Exploiting Mucosal Surfaces for the Development of Mucosal Vaccines,"Vaccine, 2011, 29:8506-8511.

Michael Vajdy, et al., "Mucosal Adjuvants and Delivery Systems for Protein-, DNA- and RNA-based Vaccines," Immunology and Cell Biology, 2004, 82: 617-627.

Wan-Ling Chiu, et al., "Engineered GFP as a Vital Reporter in Plants," Current Biology, 1996, 6(3): 325-330.

* cited by examiner

Pg1.2
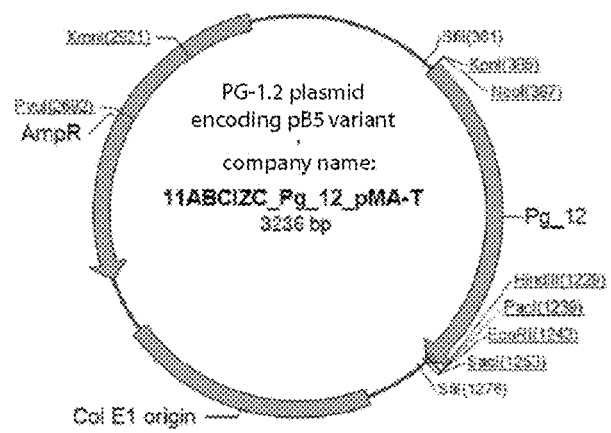
Pg2.2
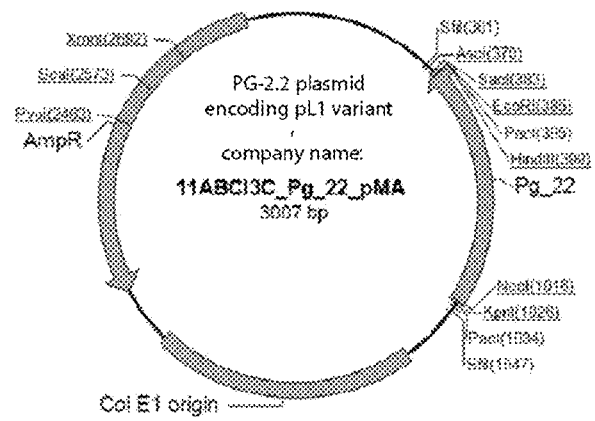
Pg3.2
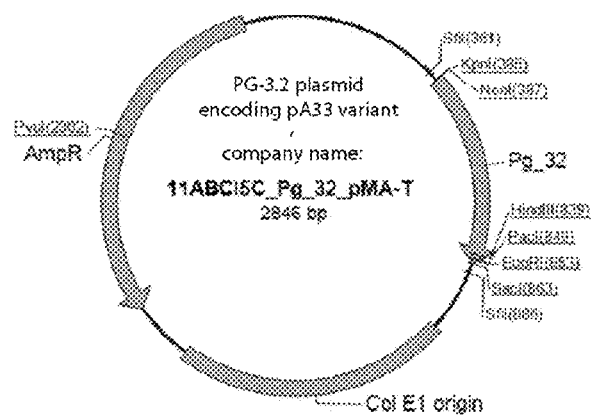
FIG. 1A

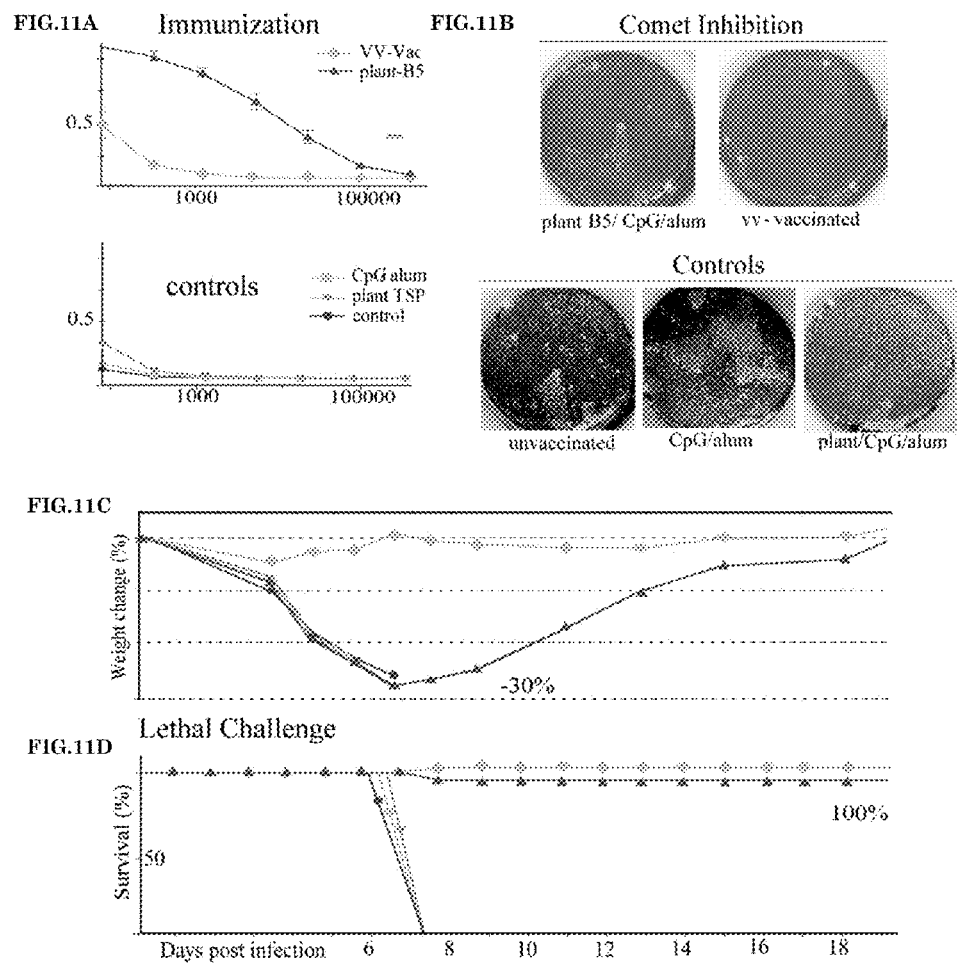

METHODS AND COMPOSITIONS TO PRODUCE VACCINES AGAINST SMALLPOX IN PLANTS

CROSS REFERENCE TO RELATED APPLICATION

This application claims priority from U.S. provisional application No. 61/614,167 filed Mar. 22, 2012, which is incorporated by reference as if fully set forth.

INCORPORATED SEQUENCE LISTING

The sequence listing electronically filed with this application, titled "Sequence Listing," was created on Mar. 22, 2013 and has a size of 16,126 bytes. This sequence listing is incorporated by reference herein as if fully set forth.

FIELD OF INVENTION

The present application relates to methods and compositions to produce immunogenic proteins conferring immunity against smallpox in a subject. In particular, the present application is directed to transgenic plants comprising recombinant smallpox antigenic proteins, expression cassettes comprising nucleic acids encoding the proteins thereof, methods for producing plant-derived immunogenic compositions against poxvirus, and methods of immunizing subjects with plant-derived compositions.

BACKGROUND

The World Health Organization declared smallpox eradicated in 1980, but the threat of smallpox used as a biological weapon still exists (Henderson, 1999 Science 283: 1279). Live smallpox vaccine is available for high-risk populations but it has serious side effects and is not considered safe for recipients with compromised immunity, pregnant women, elderly and infants. Currently, the risk of vaccination with live small pox vaccine must be weighed against the risk of fatal smallpox exposure. Even for high risk populations, live smallpox vaccine is not considered safe. A need exists for safer and more effective vaccines against smallpox (Enserink, 2004 Science 304: 809).

SUMMARY

An aspect of the invention relates to an expression cassette that includes a first polynucleotide encoding a first immunogenic protein and a second polynucleotide encoding a second immunogenic protein. Each of the first immunogenic protein and the second immunogenic protein is independently selected from the group consisting of: an L1 protein, a B5 protein and an A33 protein. The protein selected as the first immunogenic protein differs from the protein selected as the second immunogenic protein.

In another aspect, the invention relates to a transgenic plant that includes an expression cassette. The expression cassette includes a first polynucleotide encoding a first immunogenic protein and a second polynucleotide encoding a second immunogenic protein. Each of the first immunogenic protein and the second immunogenic protein is independently selected from the group consisting of: an L1 protein, a B5 protein and an A33 protein. The protein selected as the first immunogenic protein differs from the protein selected as the second immunogenic protein.

In another aspect, the invention relates to a method for producing a plant-derived immunogenic composition. The method includes contacting a plant with a first polynucleotide encoding a first immunogenic protein and a second polynucleotide encoding a second immunogenic protein. The method further includes culturing the plant under conditions effective for expressing the first immunogenic protein and the second immunogenic protein. Each of the first immunogenic protein and the second immunogenic protein is capable of eliciting an immune response in a subject against poxvirus.

In another aspect, the invention relates to a method of immunizing a subject against poxvirus. The method includes engineering a plant that includes a polynucleotide encoding at least one protein capable of eliciting an immune response against poxvirus in a subject. The method includes culturing the plant under conditions effective for expression of the at least one protein. The method includes preparing an immunogenic composition from the plant. The method also includes administering the immunogenic composition to the subject.

BRIEF DESCRIPTION OF THE DRAWINGS

The following detailed description of embodiments will be better understood when read in conjunction with the appended drawings. For the purpose of illustration, there are shown in the drawings embodiments which are presently preferred. It is understood, however, that the invention is not limited to the precise arrangements and instrumentalities shown. In the drawings:

FIG. 1A illustrates a schematic drawing of PMA and PMA-T based vectors used for sub-cloning of the Pg1.2, Pg2.2 and Pg3.2 polynucleotides.

FIG. 11A illustrates IgG titers detected in sera from mice immunized with live Vaccinia virus (VV; diamond) or with plant B5 protein in Cpg/alum (triangle). Control groups were injected with an adjuvant alone (CpG/alum; rectangle) or wild type plant TSP extracts (triangle), or left unvaccinated (control).

FIG. 11B illustrates characteristic comets formed by VV. Comet formation was altered by the B5 antibodies present in sera from mice immunized with B5 protein together with the CpG/alum adjuvant (upper panel, left).

FIGS. 11C-11D illustrate weight loss (FIG. 11C) and survival rate (FIG. 11D) after lethal intranasal challenge with VV conducted three weeks after the last i.m. vaccination (or 7 weeks after the single vaccinia vaccination by tail scarification). Those mice with a >30% initial weight loss (or morbid) were sacrificed. The symbols in these graphs correspond to the symbols in FIG. 11A.

DETAILED DESCRIPTION OF EMBODIMENTS

Figure 1B:
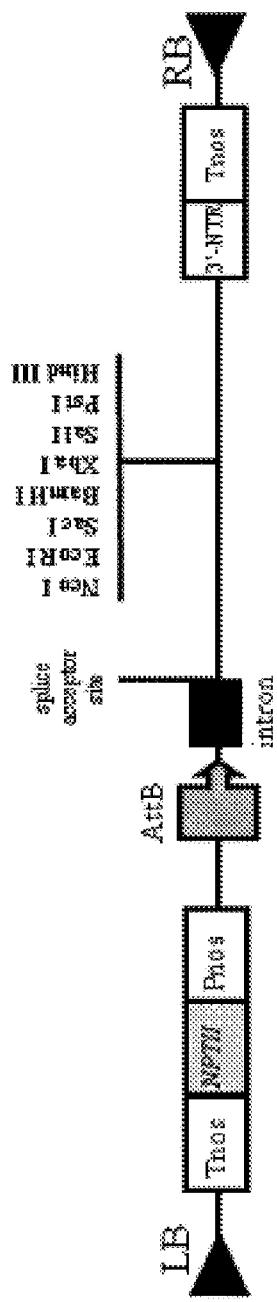
FIG. 1B illustrates a schematic drawing of a Magnicon pICH11599 vector for transient expression.

Certain terminology is used in the following description for convenience only and is not limiting. The words "right," "left," "top," and "bottom" designate directions in the drawings to which reference is made.

As used herein, the words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

The embodiments discussed herein provide technologies to express L1, B5 and A33 immunogenic proteins in plants. As used herein, the term "immunogenic proteins" refers to proteins that are antigens, including, but not limited to, virus coat proteins or membrane proteins. Production of immunogenic proteins in plants may be easily scaled up. The potential to produce large quantities of immunogenic proteins may be useful for preindustrial and industrial scale production, during threats of bioterrorism and continuous outbreaks of orthopoxvirus diseases. The plant-derived compositions may also be produced at a lower cost compared to traditional vaccines. An advantage of plant-derived immunogenic compositions is that these compositions are free of mammalian pathogens (Golovkin, 2011 Human Vaccine 7:303; Golovkin, 2011 Chpt. 14; Bioprocess Sci and Techn Nova; Golovkin et al., 2007 Proc Natl Acad Sci USA 104:6864, all of which are incorporated herein by reference as if fully set forth).

An embodiment herein provides an expression cassette that includes one or more polynucleotide sequences encoding immunogenic proteins capable of eliciting an immune response against poxvirus in a subject. An expression cassette may be a nucleic acid construct, generated recombinantly or synthetically, with a series of specified nucleic acid elements, which permit transcription of a particular nucleic acid in a plant cells and plant tissues. The expression cassette may include an open reading frame encoding an antigenic polypeptide.

In an embodiment an expression cassette preferably includes a first polynucleotide encoding a first immunogenic protein and a second polynucleotide encoding a second immunogenic protein. Each of the first immunogenic protein and the second immunogenic protein may be independently selected from the group consisting of an L1 protein, a B5 protein and an A33 protein. The protein selected as the first immunogenic protein may differ from the protein selected as the second immunogenic protein. The first and the second immunogenic proteins are capable of eliciting an immune response against poxvirus in a subject.

The first polynucleotide or the second polynucleotide preferably includes a sequence optimized for protein expression in plants. The optimized sequence may enhance expression of an exogenous polynucleotide in plants. The optimized sequence may include plant optimized codon sequences as well as plant regulatory sequences, promoters, enhancers, and termination sequences.

The first polynucleotide may include, consist essentially of, or consist of a sequence with at least 70, 72, 75, 80, 85, 90, 91, 92, 93, 94, 95, 96, 97, 98, 99, or 100% identity to a reference sequence selected from the group consisting of SEQ ID NOS: 6-11 and 14-19. Preferably, the first polynucleotide includes, consists essentially of, or consists of a sequence with at least 90% identity to a reference sequence selected from the group consisting of SEQ ID NOS: 6-11 and 14-19.

The second polynucleotide may include, consist essentially of, or consist of a sequence with at least 70, 72, 75, 80, 85, 90, 91, 92, 93, 94, 95, 96, 97, 98, 99, or 100% identity to a reference sequence selected from the group consisting of SEQ ID NOS: 6-11 and 14-19. Preferably, the second polynucleotide includes, consists essentially of, or consists of a sequence with at least 90% identity to a reference sequence selected from the group consisting of SEQ ID NOS: 6-11 and 14-19.

The first polynucleotide may include a sequence capable of hybridizing under conditions of moderate stringency to a reference sequence selected from the group consisting of SEQ ID NOS: 6-11 and 14-19. The second polynucleotide sequence may include a sequence capable of hybridizing under conditions of moderate stringency to a reference sequence selected from the group consisting of SEQ ID NOS: 6-11 and 14-19. The SEQ ID NO of the sequence selected as the second polynucleotide may differ from the SEQ ID NO of the sequence selected as the first polynucleotide.

The expression cassette may further include a third polynucleotide encoding a third immunogenic protein. The third immunogenic protein is capable of eliciting an immune response in a subject against poxvirus. The third immunogenic protein may be selected from the group consisting of: an L1 protein, a B5 protein and an A33 protein. The protein selected as the third immunogenic protein may differ from the protein selected as the first immunogenic protein and the second immunogenic protein.

The third polynucleotide may include, consist essentially of, or consist of a sequence with at least 70, 72, 75, 80, 85, 90, 91, 92, 93, 94, 95, 96, 97, 98, 99, or 100% identity to a reference sequence selected from the group consisting of SEQ ID NOS: 6-11 and 14-19. Preferably, the third polynucleotide includes, consist essentially of, or consists of a sequence with at least 90% identity to a reference sequence selected from the group consisting of SEQ ID NOS: 6-11 and 14-19. The SEQ ID NO of the sequence selected as the third polynucleotide may differ from the SEQ ID NO of the sequence selected as the second polynucleotide and the third polynucleotide.

The third polynucleotide may include a sequence capable of hybridizing under conditions of moderate stringency to a reference sequence selected from the group consisting of SEQ ID NOS: 6-11 and 14-19.

The polynucleotide sequences encoding immunogenic proteins may include naturally occurring, isolated, recombinant or synthetic sequences. Variants and fragments of polynucleotide sequences encoding L1, A33 and B5 immunogenic proteins may hybridize to the reference sequences under low, moderate or high stringency conditions.

In an embodiment, polynucleotides are provided having a sequence as set forth in any one of the nucleic acids listed herein or the complement thereof. In an embodiment, polynucleotides having a sequence that hybridizes to a nucleic acid having the sequence of any nucleic acid listed herein or the complement thereof are provided. In an embodiment, the hybridization conditions are low stringency conditions. In an embodiment, the hybridization conditions are moderate stringency conditions. In an embodiment, the hybridization conditions are high stringency conditions. Examples of hybridization protocols and methods for optimization of hybridization protocols are described in the following book: in Green and Sambrook. Molecular Cloning: a Laboratory Manual. 4th ed. Spring Harbor, N.Y: Cold Spring Harbor Laboratory Press, which is incorporated by reference in as if fully set forth.

Moderate conditions may be as follows: filters loaded with DNA samples are pretreated for 2-4 hours at 68° C. in a solution containing 6× citrate buffered saline (SSC; Amresco, Inc., Solon, Ohio), 0.5% sodium dodecyl sulfate (SDS; Amresco, Inc., Solon, Ohio), 5×Denhardt's solution (Amresco, Inc., Solon, Ohio), and denatured salmon sperm (Invitrogen Life Technologies, Inc. Carlsbad, Calif.). Hybridization is carried in the same solution with the following modifications: 0.01 M EDTA (Amresco, Inc., Solon, Ohio), 100 μg/ml salmon sperm DNA, and 5-20×$10^6$ cpm $^{32}$P-labeled or fluorescently labeled probes. Filters are incubated in hybridization mixture for 16-20 hours and then washed for 15 minutes in a solution containing 2×SSC and 0.1% SDS. The wash solution is replaced for a second wash with a solution containing 0.1×SSC and 0.5% SDS and incubated an additional 2 hours at 20° C. to 29° C. below Tm (melting temperature in ° C.), where:

$$Tm=81.5+16.61\ \mathrm{Log}_{10}([Na^+]/(1.0+0.7[Na^+]))+0.41(\%[G+C])-(500/n)-P-F;$$

[Na+]=Molar concentration of sodium ions;

%[G+C]=percent of G+C bases in DNA sequence;

N=length of DNA sequence in bases;

P=a temperature correction for % mismatched base pairs (~1° C. per 1% mismatch);

F=correction for formamide concentration (=0.63° C. per 1% formamide).

Filters are exposed for development in an imager or by autoradiography.

Low stringency conditions refers to hybridization conditions at low temperatures, for example, between 37° C. and 60° C., and the second wash with higher [$Na^+$] (up to 0.825M) and at a temperature 40° C. to 48° C. below Tm. High stringency refers to hybridization conditions at high temperatures, for example, over 68° C., and the second wash with [Na+]=0.0165 to 0.0330M at a temperature 5° C. to 10° C. below Tm.

In an embodiment, polynucleotides having a sequence that has at least 75, 80, 85, 90, 91, 92, 93, 94, 95, 96, 97, 98, 99 or 100% identity along its length to a contiguous portion of a nucleic acid having any one of the sequences set forth herein or the complements thereof are provided. The contiguous portion may be the entire length of a sequence set forth herein or the complement thereof.

In an embodiment, isolated nucleic acids, polynucleotides, or oligonucleotides are provided having a portion of the sequence as set forth in any one of the nucleic acids listed herein or the complement thereof. These isolated nucleic acids, polynucleotides, or oligonucleotides are not limited to but may have a length in the range from 10 to full length, 10 to 1000, 10 to 900, 10 to 800, 10 to 10 to 600, 10 to 500, to 400, 10 to 300, 10 to 200, 10 to 100, 10 to 90, 10 to 80, 10 to 70, 10 to 60, 10 to 50, to 40, 10 to 35, 10 to 30, 10 to 25, 10 to 20, 10 to 15, or 20 to 30 nucleotides or 10, 15, or 25 nucleotides. An isolated nucleic acid, polynucleotide, or oligonucleotide having a length within one of the above ranges may have any specific length within the range recited, endpoints inclusive. The recited length of nucleotides may start at any single position within a reference sequence (i.e., any one of the nucleic acids herein) where enough nucleotides follow the single position to accommodate the recited length. In an embodiment, a hybridization probe or primer is 85 to 100%, 90 to 100%, 91 to 100%, 92 to 100%, 93 to 100%, 94 to 100%, 95 to 100%, 96 to 100%, 97 to 100%, 98 to 100%, 99 to 100%, or 100% complementary to a nucleic acid with the same length as the probe or primer and having a sequence chosen from a length of nucleotides corresponding to the probe or primer length within a portion of a sequence as set forth in any one of the nucleic acids listed herein. In an embodiment, a hybridization probe or primer hybridizes along its length to a corresponding length of a nucleic acid having the sequence as set forth in any one of the nucleic acids listed herein. In an embodiment, the hybridization conditions are low stringency. In an embodiment, the hybridization conditions are moderate stringency. In an embodiment, the hybridization conditions are high stringency.

The variants or fragments of the polynucleotides encoding the immunogenic proteins may be identified, isolated or synthesized by any known methods. For optimal expression in a host cell, a polynucleotide sequence encoding an L1 protein, an A33 protein and a B5 protein may be codon-optimized by adapting the codon usage to that most preferred in host genes. In case the host is a plant, codon usage may be optimized to native plant genes (Itakura et al. 1977 Science 198:1056; Bennetzen et al. 1982 J Mol Chem 257: 3026) using codon usage tables. Codon usage table are publicly available for various plant species (Nakamura et al. 2000 Nucl Acid Res 28: 292).

In one embodiment, at least one of the first immunogenic protein or the second immunogenic protein may be an L1 protein, an A33 protein, or a B5 protein. The first immunogenic protein or the second immunogenic protein may be a variant protein. The variant may be derived from poxvirus. Poxvirus may include but not limited to: vaccinia virus, variola virus, monkeypox virus, raccoon poxvirus, skunk poxvirus, camelpox virus, ectromelia virus, cowpox virus, taterapox virus and volepox virus. A variant may include an amino acid sequence with at least 70, 75, 80, 85, 90, 91, 92, 93, 94, 95, 96, 97, 98, 99 or 100% identity to an amino acid sequence of at least one of an L1 protein, an A33 and a B5 protein.

Determining percent identity of two amino acid sequences or two nucleic acid sequence may include aligning and comparing the amino acid residues or nucleotides at corresponding positions in the two sequences. If all positions in two sequences are occupied by identical amino acid residues or nucleotides then the sequences are said to be 100% identical. Percent identity may be measured by the Basic Local Alignment Search Tool (BLAST; Altschul, S. F., Gish, W., Miller, W., Myers, E. W. & Lipman, D. J, 1990 "Basic local alignment search tool." J. Mol. Biol. 215:403-410, which is incorporated herein by reference as if fully set forth).

Variants may include conservative amino acid substitutions, i.e., substitutions with amino acids having similar properties. Conservative substitutions may be a polar for polar amino acid (Glycine (G), Serine (S), Threonine (T), Tyrosine (Y), Cysteine (C), Asparagine (N) and Glutamine (Q)); a non-polar for non-polar amino acid (Alanine (A), Valine (V), Thyptophan W), Leucine (L), Proline (P), Methionine (M), Phenilalanine (F)); acidic for acidic amino acid Aspartic acid (D), Glutamic acid (E)); basic for basic amino acid (Arginine (R), Histidine (H), Lysine (K)); charged for charged amino acids (Aspartic acid (D), Glutamic acid (E), Histidine (H), Lysine (K) and Arginine (R)); and a hydrophobic for hydrophobic amino acid (Alanine (A), Leucine (L), Isoleucine (I), Valine (V), Proline (P), Phenilalanine (F), Tryptophan (W) and Methionone (M)). Conservative nucleotide substitutions may be made in a nucleic acid sequence by substituting a codon for an amino acid with a different codon for the same amino acid. Variants may include non-conservative substitutions.

In an embodiment, fragments of an L1 protein, an A33 protein or a B5 protein are provided. Fragments may include 100, 150, 200, 300, 400, 600, contiguous amino acids or more, such as 700.

The functionality of an immunogenic protein, variants or fragments thereof, may be determined using any methods. The functionality may include conferring immunogenic properties. The functionality may be assessed using animal models. The functionality of a protein, or variants, or fragments thereof, may be assessed based on an ability to elicit an immune response and generate an antibody specifically binding the protein when administered to an animal. The functionality may be assessed based on an ability to inhibit poxvirus. Assessment of functionality of proteins may include a virus neutralization assay which includes incubation of a virus titer with serial dilutions of serum obtained from an animal after periodic administering of an immunogenic protein and quantifying the amount of the remaining virus by, e.g., plaque "comet inhibition" assay (Isaacs et al., 1992 J Virol 66:7217; Aldaz-Carroll et al., 2005 J. Virol. 79:6260; Xiao et al., 2006 Vaccine 25:1214, all of which are incorporated by reference herein as if fully set forth).

In an embodiment, an isolated polynucleotide sequences encoding L1 immunogenic protein and at least one of A33 and B5 immunogenic proteins may be provided in an expression cassette suitable for expression in plant cells, tissues organs and/or whole organism. The expression cassette may further include a regulatory element operably linked to at least one of the first polynucleotide, the second polynucleotide or the third polynucleotide. In this context, operably linked means that the regulatory element imparts its function on the polynucleotide. For example, a regulatory element may be a promoter, and the operably linked promoter would control overexpression of the polynuceotide.

The expression of any one of the first, the second or the third polynucleotide sequence in the expression cassette may be under the control of a promoter which provides for transcription of the polynucleotides in a plant. The promoter may be a constitutive promoter or, tissue specific, or an inducible promoter. A constitutive promoter may provide transcription of the polynucleotides throughout most cells and tissues of the plant and during many stages of development but not necessarily all stages. An inducible promoter may initiate transcription of the polynucleotide sequences only when exposed to a particular chemical or environmental stimulus. A tissue specific promoter may be capable of initiating transcription in a particular plant tissue. Plant tissue may be, but is not limited to, a stem, leaves, trichomes, anthers, or seed. Constitutive promoter may be, but is not limited to, the Cauliflower Mosaic Virus (CAMV) 35S promoter, the Cestrum Yellow Leaf Curling Virus promoter (CMP) or the CMP short version (CMPS), the Rubisco small subunit promoter, and the maize ubiquitin promoter.

The regulatory element may be a terminator, which terminates transcription and may be included at the 3' end of a transcriptional unit of the expression cassette. The terminator may be derived from a variety of plant genes. The terminator may be derived from the nopaline synthase or octopine synthase genes of *Agrobacterium tumefaciens*.

In an embodiment, an expression cassette may be incorporated into a plasmid, chromosome, mitochondrial DNA, plastid DNA, virus or nucleic acid fragment. The expression cassette may be inserted in a vector. Suitable vectors may be cloning vectors, transformation vectors, expression vectors, virus-based vectors. The expression cassette portion of an expression vector may include, among other sequences, a nucleic acid to be transcribed and a promoter.

For stable plant transformation, a vector may be a T-DNA binary vector or a cointegrate vector. A vector may include multiple cloning sites to facilitate molecular cloning and selection markers to facilitate selection. A selection marker may be, but is not limited to, a neomycin phosphotransferase (npt) gene conferring resistance to kanamycin, a hygromycin phosphotransferase (hpt) gene conferring resistance to hygromycin, and a bar gene conferring resistance to phosphinothricin.

A vector may be a viral-based vector designed for transient expression of immunogenic proteins in a plant. As used herein, the term a "virus-based vector" refers to a virus modified to function as an expression vector. Virus-based vectors may allow for the rapid, high level, transient expression of proteins in whole plants. For instance, tobacco mosaic virus (TMV)-based or potato virus X (PVX)-based vectors may express the high levels of foreign protein in plants. TMV vectors may be used to produce different kinds of proteins in plants including allergens, antibodies or antibody fragments, and vaccine candidates. The term "transient expression" refers to the expression of the transgene, or exogenous gene delivered into a host cell, e.g., a plant cell, and not integrated in the host's cell chromosome. Expression from extra-chromosomal transgenes may be detected after a period of time following a DNA-delivery. Virus-based vectors may be used to carry and express exogenous genes. Viral-based vectors may replicate and spread systemically within the plant host and lead to high levels of protein accumulation.

In an embodiment, a viral-based vector may be, but is not limited to, a tobacco mosaic virus (TMV)-based vector and a potato virus X (PVX)-based vector. A viral-based vector may be a "Magnifection" system described by Giritch et al. 2006 Proc Natl Acad Sci USA 103: 14701; Marillonnet et al. 2005 Nature Biotech 23: 718; and Marillonnet et al. 2004 Proc Natl Acad Sci USA 101: 6852, all of which are incorporated herein as if fully set forth.

Features of "Magnifection" system are shown in Table 1. The "Magnifection" system may be used to test and produce biopharmaceuticals "on demand" in large quantities and at low cost.

TABLE 1

Transient plant technology: features of "magnification"

| Expression system | Time to mg of antigen | Time to g of antigen |
|---|---|---|
| Mammalian cell culture | 2-6 months | 6-12 months |
| Transgenic animals | >12 months | >12 months |
| Stable transgenic plants | 12 months | >24 months |
| Magnifection | 14 days | 14-20 days |

Methods for delivering viral vectors into plants and production of heterologous proteins thereof are known in the art. See U.S. Pat. Nos. 5,889,190; 5,889, 191; 5,316,931; 5,589,367; 7,667,092; 7,670,801; 7,763,458; 8,093,458; and 8,003,381, all of which are incorporated by reference herein in their entirety. Viral vectors may be T-DNA vectors. T-DNA vectors may be delivered to a plant by any method.

Plants may be infiltrated with a diluted *Agrobacterium* suspension carrying T-DNAs encoding viral replicons. The resultant plants may have a high copy number of RNA molecules that encode immunogenic proteins. Immunogenic proteins may be produced in plants rapidly, in 10-14 days. Increasing the volume of biomass containing immunogenic proteins may not require changes in growing conditions. Features of transient expression system may include non-integration of external genes into the plant genome, and thus reducing or eliminating the risk of releasing transgene into environment through pollen, seeds, or other routes. Further, no intact and replication-competent virus may be produced, thus, reducing or eliminating the risk of virus mediated spreading of the recombinant genes. Protein production may be performed in a closed indoor setting (Golovkin et al., 2007 Proc Natl Acad Sci USA 104:6864, which is incorporated by reference herein as if fully set forth).

In an embodiment, a transgenic plant including any of the expression cassettes herein is provided. The transgenic plant may be any plant, or a part of a plant. The part of a plant may be, but is not limited to, a stem, a leaf, a flower, a seed, or a callus. The transgenic plant may be a progeny, or descendant of a transgenic plant. The transgenic plant may be obtained through crossing of a transgenic plant and a non-transgenic plant as long as it retains the expression cassette as described above. The transgenic plant may be a crop cultivated for purposes of obtaining food, feed or plant derived products including carbohydrates, oil and medicinal ingredients. A crop plant may be selected from the group consisting of: tomato, tobacco, pepper, eggplant, lettuce, sunflower, collard, oilseed rape, broccoli, cauliflower and cabbage crops, cucumber, melon, watermelon, pumpkin, squash, peanut, soybean, cotton, beans, cassava, potatoes, sweet potato, okra, carrot, barley, pearl millet, wheat, rye, buckwheat, sorghum, rice. The transgenic plant may include forage grasses. The transgenic plant may include tree species and fleshy fruit species. The transgenic plants may include grapes, peaches, plums, cherries, strawberries, cranberries, blueberries, mangos, and bananas.

The transgenic plant may be a medicinal plant. A medicinal plant may be a plant thought to have medicinal property and used in herbalism. The medicinal plant may be selected from the group consisting of: *Caragana sinica, Codonopsis pilosulae, Hedyotis diffusa, Houttuynia cordata, Lonicera japonica, Morinda officinalis, Oenothera odorata, Kalanchoe pinnata, Echinacea angustifolia, Calendula officinalis* and *Arthemis nobilis*. The medicinal plant may be Yerba Santa. The transgenic Yerba Santa plant was described in U.S. Pat. No. 8,148,609, issued Apr. 3, 2012; U.S. patent application Ser. No. 13/414,841, filed Mar. 8, 2012, all of which are incorporated herein by reference as if fully set forth.

In an embodiment, a method for producing a plant-derived immunogenic composition against poxvirus is provided. A method may include contacting a plant with a first polynucleotide encoding a first immunogenic protein and a second polynucleotide encoding second protein. The method may include contacting the plant with a third polynucleotide encoding the third immunogenic protein. The method may include culturing the plant under conditions effective for expressing the first immunogenic protein, the second immunogenic protein and/or the third immunogenic protein. The plants may be cultured under in vitro conditions. The plants may be grown in the field or in the greenhouse. The plants may express the first immunogenic protein, the second immunogenic protein and/or the third immunogenic protein under these growth conditions. The first immunogenic protein, the second immunogenic protein and/or the third immunogenic protein may be capable of eliciting an immune response in a mammal against poxvirus.

The step of contacting may include contacting with a vectors providing for stable transformation of a plant. The step of contacting may include contacting with a vector providing for transient expression in a plant. As a result of contacting, the plant may be engineered to express the first immunogenic protein, the second immunogenic and/or the third immunogenic protein. The plant may be a transgenic plant that integrates the polynucleotides into its genome. The plant may transiently express the polynucleotides and produce immunogenic proteins. The method may further include isolating and purifying the first immunogenic protein, the second immunogenic protein and/or the third immunogenic protein from the plant.

The method further may include providing an adjuvant. The adjuvant may be any adjuvant. As used herein, the term "adjuvant" refers to a pharmacological or immunological agent which when administered with an antigen nonspecifically enhances the recipient's response to that antigen. The adjuvant may be selected from the group consisting of: Alum, an oil-in-water nannoemulsion (MF59™), a glycolipid monophosphoryl lipid A (MPL®), virus-like particles (VLP), cholera toxin B subunit (CTB), montanides ISA51 and ISA720, saponines Quil-A, ISCOM and QS-21, syntax adjuvant formulation (SAF), muramyl dipeptides (MDP), immunostimulatory oligonucleotides, TLR ligands, *Escherichia coli* heat-labile exotoxin, and lipid-based adjuvants (Vajdy et al., 2004 Imm and Cell Biol 82:617; Schroder et al., 1999 Vaccine 17:2096, all of which are incorporated by reference herein as if fully set forth).

In an embodiment, the method further may include providing a pharmaceutically acceptable carrier. As used herein, the term "pharmaceutically acceptable carrier" refers to solvents, diluents, preservatives, dispersion or suspension aids, isotonic agents, thickening or emulsifying agents, solid binders, and lubricants, appropriate for the particular dosage form. The skilled artisan is aware of a variety of different carriers that may be used in formulating pharmaceutical compositions and knows techniques for the preparation thereof (See *Remington's Pharmaceutical Sciences* Ed. by Gennaro, Mack Publishing, Easton, Pa., 1995). The pharmaceutically acceptable carriers may include, but are not limited to Ringer's solution, isotonic saline, starches, potato starch, sugars, glucose, powdered tragacant, malt, gelatin, talc, cellulose and its derivatives, ethyl cellulose, sodium carboxymethyl cellulose, cellulose acetate excipients, cocoa butter, suppository waxes, agar, alginic acid, oils, cottonseed oil, peanut oil, safflower oil, sesame oil, olive oil, soybean oil, corn oil, glycols, propylene glycol, esters, ethyl laurate, ethyl oleate, buffering agents, aluminum hydroxide, magnesium hydroxide, phosphate buffer solutions, pyrogen-free water, ethyl alcohol, other non-toxic compatible lubricants, sodium lauryl sulfate, magnesium stearate, coloring agents, releasing agents, coating agents, sweetening, flavoring and perfuming agents. Pharmaceutically acceptable carriers may also include preservatives and antioxidants.

In an embodiment, method of immunizing a subject against poxvirus may be provided. The method may include engineering a plant that includes a polynucleotide encoding at least one protein capable of eliciting an immune response against poxvirus in a subject. The method may include culturing the plant under conditions effective for expression of the at least one protein. The method may include preparing an immunogenic composition from the plant. The method may include administering the immunogenic composition to the subject. The at least one protein may immunize the subject against poxvirus.

The method may include isolating and purifying the at least one protein from the plant prior to preparing the composition.

The subject may be a mammal. The mammal may be an animal or a human. The mammal may be a male or female mammal. The mammal may be a primate. The primate may be a non-human primate. The non-human primates may include but are not limited to chimpanzees, other apes and monkey species, farm animals, cattle, sheep, pigs, goats, horses, domestic mammals, dogs, cats, laboratory animals, rodents, mice, rats, guinea pigs, birds, domestic birds, wild and game birds, chickens, turkeys and other gallinaceous birds, ducks, geese. The term mammal does not denote a particular age. The mammal may include adult and newborn individuals. The immunogenic composition described herein may be used in any of the above mammals, since the immune systems of all of these mammals operate similarly.

The at least one protein may be derived from poxvirus. The at least one protein may be a membrane protein. The at least one protein may be selected from the group consisting of: L1, A33, B5, AI7, A27, A34, A56, D8, F9, F13, and H3 proteins.

In an embodiment, preparing the immunogenic composition may include providing plant-derived immunogenic compositions against poxvirus. The immunogenic compositions may include an L1 protein and at least one of an A33 protein and B5 protein produced in plants. The plant-derived immunogenic compositions may elicit an immune response in a subject. The plant-derived immunogenic compositions may further include adjuvants. The plant-derived immunogenic compositions may include pharmaceutically acceptable carriers.

In an embodiment, an immunogenic composition may be administered to a subject by any route. The immunogenic composition may be administering by at least one route selected but not limited to: intravenous, intramuscular, intraperitoneal, intradermal, mucosal, cutaneous and subcutaneous. An immunogenic composition may be introduced by injection, inhalation, oral, or intranasal route of administration. An immunogenic composition may be introduced by a parenteral or mucosal route of administration. Routes may include administering a composition rectally, intravaginally, intraperitoneally, intracisternally and or ectopically. Routes may include administering intranasally. The intranasal administration may include inhalation or nose drops. A mucosal route may include administering an immunogenic composition to any mucosal surface of the body of the recipient. Mucosal administration may differ from "systemic" or "parenteral" administration. Systemic administration may include administering compositions to a non-mucosal surface, e.g., intraperitoneal, intramuscular, sub-, or transcutaneous, intra- or transdermal, or intravenous administration. Mucosal administration may induce a mucosal immune response (Enserink, 2004 Science 304: 809, which is incorporated herein by reference as if fully set forth).

A "mucosal immune response" or "mucosal immunity" refers to the induction of a cell-mediated and/or humoral response. A cell-mediated mucosal immune response may be assessed by measuring the T cell response from lymphocytes isolated from the mucosal area and/or secretory glands. A humoral mucosal immune response may be assessed by measuring the antigen-specific antibodies present in the mucosal lavage in response to introduction of the desired antigen into the host. An immune response may be specific for the immunogenic protein with which the subject was immunized (Meeusena, 2011 Vaccine 29:8506, which is incorporated herein by reference as if fully set forth).

An immunogenic composition may be administered in a formulation with an appropriate pharmaceutically acceptable carrier in a desired dosage An immunogenic composition may be administered in liquid dosage forms. Liquid dosage forms may be prepared for nasal administration. Liquid dosage forms for nasal administration may include, but are not limited to, pharmaceutically acceptable emulsions, microemulsions, solutions, and suspensions. Liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the nasal compositions may also include adjuvants. Liquid dosage forms for nasal administration may be aqueous drops, a mist, an emulsion, or a cream.

Dosage forms for topical or transdermal administration of an inventive pharmaceutical composition may include ointments, pastes, creams, lotions, gels, powders, solutions, sprays, inhalants, or patches. Powders and sprays may contain immunogenic proteins admixed with excipients such as talc, silicic acid, aluminum hydroxide, calcium silicates, polyamide powder, or mixtures of these substances. Sprays may additionally contain customary propellants, for example, chlorofluorohydrocarbons. The immunogenic proteins may be admixed under sterile conditions with a pharmaceutically acceptable carrier and any needed preservatives or buffers as may be appropriate.

Compositions for rectal or vaginal administrations may include suppositories. Suppositories may be prepared by mixing of the immunogenic proteins of this invention with suitable non-irritating excipients or carriers such as cocoa butter, polyethylene glycol or a suppository wax. Carriers may be solid at ambient temperature but liquid at body temperature and therefore melt in the rectum or vaginal cavity and release the immunogenic proteins.

In an embodiment, the method may further include measuring an antibody titer in serum of an infected mammal, wherein an increase in antibody specific to the at least one protein in comparison to a control serum may be an indication of efficacy of the immunogenicity of the composition.

As discussed above and described in greater details in the Examples, vaccine preparations, e.g., by stable or transient expression of viral membrane antigens in plants, isolation and purification of the antigenic proteins, may be used to prepare plant-derived immunogenic compositions for immunizing subjects for resistance against poxvirus associated illnesses. In embodiments, treatments of a variety of infectious diseases arising from infection with vaccinia virus, variola virus, monkeypox virus, raccoon poxvirus, skunk poxvirus, camelpox virus, ectromelia virus, cowpox virus, taterapox virus and volepox virus are provided. Plant-derived immunogenic compositions may be useful to treat patients with compromised immunity; patients anticipating therapy involving, for example, immunosuppression and complications associated with systemic treatment with steroids, radiation therapy, anti-neoplastic drugs and anti-metabolites.

In an embodiment, a plant-derived composition may be administered to a subject to be therapeutically effective. Therapeutic efficacy may depend on effective amounts of active agents and time of administering necessary to achieve the desired result. Administering a plant-derived immunogenic composition may be a preventive measure. Administering of a plant-derived composition may be a therapeutic measure to promote immunity to the infectious agent, to minimize complications associated with the slow development of immunity especially in patients with a weak immune system, elderly or infants.

In an embodiment, the plant-derived immunogenic composition may be administerd in a therapeutically effective amount. The therapeutically effective amount may be the amount sufficient to generate appearance of antigen-specific antibodies in serum, or disappearance of disease symptoms. Disappearance of disease symptoms may be assessed by decrease of virus in feces or in bodily fluids or in other secreted products. The plant-derived compositions may be administered using any amount and any route of administration effective for generating an antibody response.

The exact dosage may be chosen by the physician based on a variety of factors and in view of individual patients. Dosage and administration may be adjusted to provide sufficient levels of the active agent or agents or to maintain the desired effect. For example, factors which may be taken into account include the type and severity of a disease; age and gender of the patient; drug combinations; and an individual response to therapy.

Therapeutic efficacy and toxicity of active agents in a composition may be determined by standard pharmaceutical procedures, for example, by determining the therapeutically effective dose in 50% of the population (ED50) and the lethal dose to 50% of the population (LD50) in cells cultured in vitro or experimental animals. Plant-derived immunogenic compositions may be evaluated based on the dose ratio of toxic to therapeutic effects (LD59/ED50), called the therapeutic index, the large value of which may be used for assessment. The data obtained from cell and animal studies may be used in formulating a dosage for human use.

The therapeutic dose shown in examples herein may be at least one microgram (1 μg), or about 3×1 μg, or about 10×1 μg unit of antigen/dose/animal. As plant-based vaccines may be readily produced and inexpensively engineered and designed and stored, greater doses for large animals may be economically feasible. For an animal several orders of magnitudes larger that the experimental animals used in examples herein, the dose may be easily adjusted, for example, to about 3×10×1 μg, or about 3×20×1 μg, or about 3×30×1 μg for animals such as humans and small agricultural animals. However, doses of about 3×40×1 μg, 3×50×1 μg or even about 3×60×1 μg, for example, for a high value zoo animal or agricultural animal such as an elephant, may be provided. For preventive immunization, or periodic treatment, or treatment of a small wild animal, smaller doses such as less than about 3×1 μg, 1 μg and less than about ½ 1 μg per dose, may be provided (Portocarrero, 2008 Vaccine 26: 5535, which is incorporated herein by reference as if fully set forth).

A skilled person will recognize that many suitable variations of the methods may be substituted for or used in addition to those described above and in the claims. It should be understood that the implementation of other variations and modifications of the embodiments of the invention and its various aspects will be apparent to one skilled in the art, and that the invention is not limited by the specific embodiments described herein and in the claims. The present application mentions various patents, scientific articles, and other publications, each of which is hereby incorporated herein in its entirety by reference.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1

Orthopoxvirus Antigens A33, B5, L1 Optimized for Plant Expression

A full extracellular antigenic domain (amino acids 20-275) of the vaccinia virus (VV) strain WR that contains major neutralization epitopes of the B5 glycoprotein (42 kDa) was initially selected for optimization. The B5 expression cassettes were designed to include C-terminal KDEL signals for ER targeting, c-Myc or His6 tags. Further optimization of the B5 extracellular antigenic domain that had no signal peptide transmembrane domain and cytoplasmic tail (Gene VACWR187) resulted in Pg1 constructs. The vaccinia virus WR antigenic domain (amino acids 1-185) of the L1 protein (Gene VACWR088) optimized for plant expression resulted in Pg2 constructs. The vaccinia virus WR antigenic domain (amino acids 58-185) of the A33 protein (Gene VACWR156) optimized for plant expression resulted in pG3 constructs. All constructs were optimized in a stepwise fashion as described in Table 2 using ELISA and Western blots for quantitation and detection of the antigens.

TABLE 2

Stepwise optimization of the B5, L1 and A33 antigens for plant expression

| Variable | Outcome |
|---|---|
| 1. Sequence analysis and optimization for expression in *Nicotiana benthamiana* | Plant codons, cryptic intron splice sites, and poly A signals were introduced in the nucleic acid sequences of B5, L1 and A33 |
| 2. Days post-infiltration | Tested expression of the sequences in plants 6-14 days post-infiltration. |
| 3. ER retention signal | Tested expression of the sequences with and without C-terminal KDEL |
| 4. ER localization signal | Tested expression of the sequences the with and without barley alpha amylase and tobacco calreticulin signal sequences |
| 5. Affinity tags | Tested expression and recovery of the sequences with C-terminal cMyc and His6 tags |
| 6. *N. bethamiana* glycosylation knock-out mutants | Tested expression and functionality of the sequences in the glycosylation knockout mutants and wild type *N. benthamina* |

Using the strategies outlined in Table 2, the nucleic acid sequences encoding the three vaccinia virus antigenic proteins were optimized for the plant-specific expression. The polynucleotides optimized and synthesized for expression in a certain host were named as the Pharma Green (Pg) polynucleotides. The polynucleotides optimized and synthesized for expression in *Nicotiana benthamiana* using the GeneScript program were named Pg1, Pg1.1 (optimized B5), Pg2, Pg2.2 (optimized L1) and Pg3, Pg3.3 (optimized A33). The Invitrogen/Geneart optimization with GeneOptimizer® for expression in the *Tobacco* genus resulted in Pg1.2, Pg2.1 and Pg3.2 sequences. The polynucleotides optimized for *Homo sapiens* for expression in plants were named Pg1.3, Pg2.3 and Pg3.1 sequences. It was observed that human codon optimization tends to provide high level of protein expression in plants (Chiu et al., Current Biology, 996, 6:325, which is incorporated herein by reference as if fully set forth).

Specific restriction/ligation sites were incorporated into each nucleic acid sequence encoding the antigenic polypeptide B5, L1 and A33 for direct subcloning into the plasmid carriers providing for either transient or stable plant transformation. The unique NcoI site CCATGG was positioned at the 5' terminal region of the nucleic acid encoding the antigenic peptide followed by the Kawazaki sequence immediately before the initiation translation ATG codon 5'-CCATGGaacaaaaATG (SEQ ID NO: 1). The unique HindIII, PacI, and EcoRI sites were positioned after the stop codon at the 3' terminal region AAGCTTaattaaGAATTC-3 (SEQ ID NO: 2).

The Pg1, Pg1.1, Pg2, Pg2.2 and Pg3, Pg3.3 expression cassettes were synthesized by the GeneScript program and contained the C-terminus-specific tags (c-Myc and/or His6 tags) and the N-terminus plant-specific intracellular targeting signals. Two types of the targing signals were introduced: the plant APBP1 gene encoding an amino acid sequence MIVLSVGSASSSPIVVVFSVALLLFYFSETSLG (SEQ ID NO: 3) for the Pg1 sequence and the plant BAA gene encoding an amino acid sequence MANKHLSLSLFLVLLGLSASLASG (SEQ ID NO:4) for the Pg1.1 sequence. The original flexible linker SKSWNRAQFGS (SEQ ID NO: 23) was introduced between the His6-tags (HHHHHH SKSWNRAQFGSHHHHHH (SEQ ID NO: 5).

For Invitrogen/Geneart arrangements of the synthetic expression cassettes the same cloning sites were chosen: the unique NcoI (that harbors the ATG codon and without targeting signals); and the unique 3' HindIII, PacI, EcoRI and additional SacI sites. At the C-terminal arrangement of the cassettes: the c-Myc and His6 tags were introduced for tobacco optimization and the double His6 with intermediate c-Myc tags were introduced for human optimization for expression in plants. These sequences were followed by the endoplasmic reticulum retention signal HDEL included immediately prior the stop codon.

If the codon usage was adapted to the codon bias of the *Homo sapiens* genes, codon adaptation index (CAI) resulted in value of 0.97 was sought to be achieved that would allow high and stable expression rates in plants. Generally, CAI describes how well the codons match the codon usage preference of the target organism. Thus, a CAI of 1.0 would be a perfect match. However, a CAI of higher than 0.9 is also considered as a very good match, i.e. allowing high levels of expression.

In addition, regions of very high (>80%) or very low (<30%) GC content has been avoided where possible with an average GC content of 58%. During the optimization process the following cis-acting sequence motifs were avoided where applicable: internal TATA-boxes, chi-sites and ribosomal entry sites, AT-rich or GC-rich sequence stretches, RNA instability motifs, repeat sequences and RNA secondary structures, (cryptic) splice donor and acceptor sites in eukaryotes.

The optimization was successful: negative cis-acting sites, such as splice sites, TATA-boxes, which may negatively influence expression were eliminated. GC content was adjusted to prolong the mRNA half life.

B5/Pg1 expression cassettes. The nucleic acid sequences encoding the B5 extracellular antigenic domain of EEV B5 Vaccinia virus glycoprotein (strain WR, GI:29692293) that has no signal peptide (amino acids 20-275), transmembrane domain and cytoplasmic tail, harbors three N-linked glycosylation sites located within the short consensus repeats (SCR2) and includes four modular SCR domains (amino acids 20-237) and the stalk region (amino acids 238-275) harboring sites of major neutralization epitopes was optimized for expression in plants. The plant optimized sequence was named pB5 (the plant optimized B5), Pg1 and Pg1.2. The Pg1 and Pg1.1 expression cassettes (GeneScript) are as follows.

```
SEQ ID NO: 6 is a 981 bp nucleic acid sequence
encoding the Pg 1 protein (314 aa):
CCATGGCTTGAAACAAAAATGATTGTGCTTTCTGTGGGATCTGCTTCT

TCTAGTCCTATCGTGGTGGTTTTCTCTGTGGCATTACTCCTCTTCTATT

TCTCTGAAACATCTTTAGGTTGTACCGTTCCTACTATGAATAACGCTAA

GTTGACTAGTACAGAGACCTCTTTTAATGATAAGCAAAAGGTTACTTTC

ACATGTGATCAGGGATACCATTCTTCAGATCCTAATGCAGTGTGCGAGA

CTGATAAGTGGAAATATGAAAACCCTTGTAAGAAAATGTGCACAGTTTC

AGATTACATCAGTGAGCTCTACAATAAGCCTCTCTATGAAGTGAACTCT

ACCATGACTCTTTCATGTAATGGTGAAACAAAGTACTTTAGATGCGAAG

AAAAGAATGGTAACACCTCATGGAATGATACAGTTACCTGTCCTAACGC

TGAGTGCCAACCACTTCAGTTGGAACATGGTTCATGTCAACCAGTGAAG

GAGAAGTACAGTTTCGGAGAATACATGACAATTAATTGTGATGTTGGTT

ACGAAGTGATTGGAGCTAGTTATATCTCTTGCACTGCAAATAGTTGGAA

CGTTATTCCTTCTTGTCAACAGAAGTGCGATATGCCATCACTTAGTAAT

GGTTTGATCTCTGGATCAACATTTTCTATTGGTGGAGTTATCCACCTTT

CATGCAAGAGTGGTTTCACTTTGACAGGATCACCAAGTTCTACTTGTAT

TGATGGAAAGTGGAATCCTGTTCTTCCAATCGCGTGAGGACCAACGAA

GAGTTTGATCCTGTTGATGATGGACCAGATGATGAGACTGATCTTTCTA

AGCTCTCAAAAGATGTTGTGCAATACGAACAGGAGATTGAATCTTTGGA

AGCAACTTATCATCACCATCACCACCACTCAAAAAGTTGGAATAGAGCA

CAGTTCGGTTCACATCATCATCATCATCACTAAAAGCTTAATTAAGAAT

TC

SEQ ID NO: 7 is a 949 bp nucleic acid sequence
encodingthe Pg1.1 (305 aa):
CCATGGAACAAAATGGCTAACAAACACTTATCACTCTCACTCTTTCT

CGTGCTCCTTGGACTCTCCGCTTCACTTGCTTCTGGATGTACTGTGCCT

ACTATGAATAACGCTAAACTTACTAGTACAGAGACTTCCTTTAACGATA

AGCAAAAGGTTACATTCACTTGTGATCAGGGATACCATTCTTCAGATCC

AAATGCAGTGTGCGAGACTGATAAGTGGAAATATGAAAACCCTTGTAAG

AAAATGTGCACTGTTTCTGATTACATCTCAGAGCTCTACAACAAACCAC

TCTATGAAGTGAACAGTACAATGACTTTGTCCTGTAATGGAGAGACAAA

GTACTTTAGATGCGAAGAGAAAAATGGTAACACTTCTTGGAATGATACA

GTTACTTGTCCAAACGCTGAGTGCCAACCTCTTCAGTTGGAACATGGAT

CATGTCAACCTGTGAAGGAGAAGTACAGTTTCGGTGAATACATGACAAT

CAACTGTGATGTTGGATACGAAGTGATCGGTGCTTCTTATATTTCATGC

ACTGCAAATAGTTGGAACGTTATTCCATCTTGTCAACAGAAGTGCGATA

TGCCTTCTCTTTCAAACGGATTGATAAGTGGTTCCACATTTTCTATTGG

AGGTGTTATACACCTTAGTTGTAAGTCCGGATTCACATTGACTGGTTCA

CCAAGTTCCACTTGTATAGATGGAAAATGGAATCCAGTTTTACCTATCT

GCGTGAGGACAAACGAAGAGTTTGATCCAGTTGATGATGGTCCTGATGA

TGAGACTGATTTATCTAAGCTCTCAAAAGATGTTGTGCAATACGAACAG

GAGATTGAATCACTTGAAGCAACATATCATCACCATCACCACCACTCAA

AATCCTGGAATAGGGCTCAGTTCGGAAGTCACCATCATCATCACCACTA

AAAGCTTAATTAAGAATTC
```

L1/Pg2 expression cassettes. A polynucleotide pL1 having a sequence that is 753 bp in length (GI: 29692194) encoding a portion of myristylated IMV Vaccinia virus protein was optimized for transient expression in plants that includes the 555 bp (amino acids 1-185) antigenic determinant. Following gene optimization and synthesis, variants with differences in targeting signals were named Pg2 and Pg2.2 as shown below; Pg2.1. and Pg2.3 versions with different design shown further down.

```
SEQ ID NO: 8 a 762 bp nucleic acid sequence
encoding the Pg2 protein (240 aa):
CCATGGCTTGAAACAAAAATGATTGTGCTTTCTGTGGGATCTGCTTCT

TCTAGTCCTATCGTGGTGGTTTTCTCTGTGGCATTACTCCTCTTCTATT

TCTCTGAAACATCTTTAGGTGGAGCAGCAGCATCAATCCAGACTACCGT

GAACACCTTATCAGAAAGAATCTCATCAAAACTCGAACAGGAGGCAAAC

GCATCAGCACAAACCAAGTGTGATATCGAAATCGGTAACTTCTACATCA

GACAGAATCATGGATGTAACTTAACAGTTAAAAACATGTGCTCTGCTGA

TGCAGATGCTCAACTTGATGCTGTGTTGTCAGCTGCAACTGAAACATAT

AGTGGTTTAACTCCTGAGCAAAAGGCATACGTTCCAGCTATGTTTACAG

CTGCACTCAATATTCAGACCTCAGTTAACACTGTTGTGAGGGATTTCGA

GAACTACGTGAAACAAACTTGTAACTCTTCAGCAGTTGTGGATAATAAG

TTGAAGATCCAGAACGTTATTATCGATGAATGCTACGGTGCTCCTGGAT

CTCCAACAAATCTTGAGTTCATTAACACCGGTAGTTCTAAGGGAAATTG

CGCTATTAAGGCTCTTATGCAGCTCACAACCAAGGCAACAACCCAAATC

GCACCAAAACAAGTGGCAGGTACAGGAGTTCAGCATCATCACCATCACC

ACCACTCAAAAAGTTGGAATAGAGCACAGTTCGGTTCACATCATCATCA

TCATCACTAAAAGCTTAATTAAGAATTC

SEQ ID NO: 9 is a 727 bp nucleic acid sequence
encoding the Pg2.2 protein (231 aa):
AGTGCTCTTGGGTCTTTCTGCATCCCTCGCTTCAGGTGGTGCTGCTGCT

TCTATCCAAACTACAGTTAACACTCTTTCTGAAAGAATCTCTTCAAAGT

TGGAACAAGAGGCTAATGCATCAGCTCAGACAAAGTGTGATATCGAGAT

CGGAAACTTCTACATCAGGCAAAATCATGGTTGTAACTTGACTGTTAAG
```

-continued

```
AACATGTGCAGTGCAGATGCTGATGCACAGTTAGATGCTGTGCTCAGTG

CTGCAACTGAAACATATTCCGGATTAACTCCAGAGCAAAAGGCTTACGT

TCCTGCAATGTTTACAGCTGCATTGAATATCCAGACTTCTGTTAACACA

GTTGTGAGAGATTTCGAAAACTACGTGAAGCAAACATGTAACAGTTCCG

CAGTTGTGGATAACAAACTTAAGATCCAGAACGTTATAATAGATGAATG

CTACGGAGCTCCAGGTTCTCCTACTAATCTTGAGTTCATTAACACAGGA

TCTTCAAAGGGTAATTGCGCTATCAAAGCACTTATGCAATTGACTACAA

AGGCTACTACACAAATTGCACCAAAACAGGTTGCTGGAACTGGTGTGCA

GCATCACCATCACCATCACAGTAAATCCTGGAATAGAGCACAGTTCGGT

TCACACCATCATCATCACCACTAAAAGCTTAATTAAGAATTC
```

A33/Pg3 expression cassettes. The same set of arrangements was made for Vaccinia virus EEV 185 amino acid 20.5 kDa protein encoded by 558 bp A33R gene (GI: 29692262). Recombinant protein (aa 58-185) of the ectodomain peptide A33 encoded by 385 bp region was named pA33, when expressed in plants. The optimized synthetic versions Pg 3 and Pg3.3 that differs by targeting signal arrangements are as follows.

SEQ ID NO: 10 is a 591 bp nucleic acid sequence encoding the Pg3 protein (184 aa):

CCATGGCTTGAAACAAAAATGATTGTGCTTTCTGTGGGATCTGCTTCT

TCTAGTCCTATCGTGGTGGTTTTCTCTGTGGCATTACTCCTCTTCTATT

TCTCTGAAACATCTTTAGGTAGGCTCAATCAGTGTATGTCTGCTAACGA

GGCTGCAATCACCGATGCTGCTGTGGCTGTGGCTGCTGCTTCTTCAACC

CATAGGAAAGTTGCTTCTTCAACTACACAATACGATCATAAGGAATCAT

GTAATGGTCTTTACTACCAAGGATCATGCTACATCTTACACAGTGATTA

CCAGCTCTTTTCTGATGCTAAGGCAAATTGTACAGCAGAAAGTTCTACC

TTGCCTAACAAATCTGATGTTCTTATCACTTGGTTGATCGATTACGTGG

AGGATACATGGGGTTCAGATGGAAACCCAATCACCAAAACCACTAGTGA

TTACCAAGATAGTGATGTTAGTCAAGAAGTGAGGAAGTATTTTTGCGTG

AAGACCATGAACCATCACCATCACCACCACTCAAAAAGTTGGAATAGAG

CACAGTTCGGTTCACATCATCATCATCATCACTAAAAGCTTAATTAAGA

ATTC

SEQ ID NO: 11 is a 559 bp nucleic acid sequence encoding the Pg3.3 protein (175 aa):

CCATGGAACAAAAAATGGCTAACAAACATCTCTCCCTCTCCCTCTTCTT

GGTGCTCCTCGGACTCAGTGCATCCTTGGCATCAGGTAGACTCAATCAG

TGCATGTCAGCAAATGAAGCTGCAATCACAGATGCTGCAGTTGCTGTGG

CTGCAGCTTCTTCAACTCATAGAAAGGTTGCAAGTTCCACTACACAATA

TGATCACAAAGAGAGTTGTAACGGACTTTACTACCAAGGTTCTTGCTAC

ATCCTCCATTCAGATTACCAGCTCTTTAGTGATGCAAAGGCTAATTGTA

CTGCTGAATCTTCAACATTGCCAAACAAGTCAGATGTTCTTATCACTTG

GTTGATCGATTACGTGGAGGATACATGGGGATCTGATGGTAACCCTATC

ACTAAGACTACATCTGATTACCAAGATAGTGATGTTTCCCAGGAAGTGA

-continued

GGAAGTACTTCTGCGTGAAAACAATGAACCATCACCATCACCACCACTC

TAAATCCTGGAATAGGGCACAGTTCGGTAGTCACCATCACCACCACCAT

TGAAAGCTTAATTAAGAATTC

A different set of recombinant antigenic genes includes polynucleotides optimized for expression in genus *Tobacco* (Pg1.2; 2.1; 3.2) encoding an amino acid sequence with c-Myc and single His6 tag EQKLISEEDLHHHHHHDEL (SEQ ID NO: 12) and polynucleotides codon optimized for expression in *Homo sapiens* and plants (Pg1.3; 2.3; 3.1) encoding an amino acid sequence with double His6 tags and intermediate c-Myc tags, HHHHHHEQKLISEEDLHHHHHHDEL (SEQ ID NO: 13) are shown below. Pg1.2 and Pg1.3 were designed by Invitrogen/GenArt.

SEQ ID NO: 14 is a 867 bp nucleic acid sequence encoding the Pg1.2 protein (279 aa):

CATGGGTTGCACTGTGCCTACCATGAACAACGCTAAGTTGACCAGCA

CCGAGACATCCTTCAACGATAAGCAAAAGGTGACCTTCACTTGCGATCA

GGGTTACCACAGCTCTGATCCTAATGCTGTGTGCGAGACTGATAAGTGG

AAGTACGAGAACCCTTGCAAGAAGATGTGCACCGTTAGCGATTACATCA

GCGAGCTGTACAACAAGCCTCTGTACGAGGTGAACTCTACCATGACCCT

TTCATGCAACGGTGAGACTAAGTACTTCAGGTGCGAAGAGAAGAACGGT

AACACCAGCTGGAATGATACTGTGACCTGCCCTAATGCTGAGTGCCAAC

CTCTTCAGCTTGAGCATGGTTCTTGCCAGCCTGTGAAAGAAAAGTACAG

CTTCGGTGAGTACATGACCATCAACTGTGATGTGGGTTACGAGGTGATC

GGTGCTAGCTACATTTCTTGCACCGCTAACAGCTGGAACGTGATCCCAT

CTTGTCAGCAAAAGTGCGATATGCCTAGCCTGAGCAACGGTCTGATTAG

CGGTTCTACCTTCTCTATCGGTGGTGTGATTCACCTGAGCTGCAAGTCT

GGTTTTACCCTGACTGGTAGCCCTAGCTCTACCTGCATTGATGGTAAGT

GGAACCCTGTGCTTCCTATCTGCGTGAGGACTAACGAAGAGTTCGATCC

TGTGGATGATGGTCCTGATGATGAGACTGATCTGAGCAAGCTGTCCAAG

CGATGTTGTGCAGTACGAGCAAGAGATCGAGTCTTTGGAGGCTACCTAC

GAGCAGAAGCTGATCTCTGAAGAGGATCTTCATCACCATCACCACACGA

TGAGCTGTAGAAGCTTTTAATTAAGAATTCGAGCTC

SEQ ID NO: 15 is a 772 bp nucleic acid sequence encoding the Pg1.3 protein (247 aa):

CCATGGGCTGCACCGTGCCCACCATGAACAACGCCAAGCTGACCAGC

ACCGAAACCAGCTTCAACGACAAGCAGAAAGTGACCTTCACCTGTGACC

AGGGCTACCACAGCAGCGACCCCAACGCCGTGTGCGAGACAGACAAGTG

GAAGTACGAGAACCCCTGCAAGAAAATGTGCACCGTGTCCGACTACATC

AGCGAGCTGTACAACAAGCCCCTGTACGAAGTGAACAGCACCATGACCC

TGAGCTGCAACGGCGAGACAAAGTACTTCAGATGCGAGGAAAAGAACGG

CAACACCAGCTGGAACGACACCGTGACCTGCCCCAATGCCGAGTGCCAG

CCCCTGCAGCTGGAACACGGCTCCTGCCAGCCCGTGAAAGAGAAGTACA

GCTTCGGCGAGTACATGACCATCAACTGCGACGTGGGCTACGAAGTGAT

CGGCGCCAGCTACATCAGCTGCACCGCCAACAGCTGGAATGTGATCCCT

-continued
AGCTGCCAGCAGAAATGCGACATGCCCAGCCTGAGCAACGGCCTGATCA

GCGGCAGCACCTTCAGCATCGGCGGCGTGATCCACCTGTCCTGCAAGAG

CGGCTTCACCCTGACCGGCAGCCCCAGCAGCACCTGTATCGACGGCAAG

TGGAACCCCGTGCTGCCCATCTGCGTGCGGACCCACCACCACCATCACC

ACGAGCAGAAGCTGATCAGCGAAGAGGACCTGCACCATCATCACCATCA

CGATGAGCTGTGAAAGCTTTTAATTAAGAATTCGAGCTC

SEQ ID NO: 16 is a 643 bp nucleic acid sequence
encoding the Pg2.1 protein (204 aa):
CCATGGGTGCTGCTGCTTCTATTCAGACTACCGTGAACACCCTGAGC

GAGAGGATTAGCTCTAAGTTGGAGCAAGAGGCTAACGCTTCTGCTCAGA

CCAAGTGCGATATCGAGATCGGTAACTTCTACATCAGGCAGAACCACGG

TTGCAACCTGACCGTGAAGAATATGTGCAGCGCTGATGCTGATGCTCAG

CTTGATGCTGTTCTTTCTGCTGCTACCGAGACTTACTCTGGTCTTACCC

CTGAGCAAAAGGCTTACGTGCCAGCTATGTTCACCGCTGCTCTTAACAT

TCAGACCTCTGTGAATACCGTGGTGAGGGATTTCGAGAACTACGTGAAG

CAGACCTGCAACTCTTCTGCTGTGGTGGATAACAAGCTGAAGATCCAGA

ACGTGATCATCGATGAGTGCTACGGTGCTCCTGGTTCTCCTACTAACCT

TGAGTTCATCAACACCGGTAGCAGCAAGGGAAACTGCGCTATTAAGGCT

CTTATGCAGCTGACCACTAAGGCTACCACTCAGATCGCTCCTAAGCAGG

TTGCAGGTACTGGTGTGCAAGAGCAGAAGCTGATCTCTGAAGAGGATCT

TCATCACCATCACCACCACGATGAGCTGTAGAAGCTTTTAATTAAGAAT

TCGAGCTC

SEQ ID NO: 17 is a 667 bp nucleic acid sequence
encoding the Pg2.3 protein (212 aa):
CCATGGGCGCTGCCGCCAGCATCCAGACCACCGTGAACACCCTGAGC

GAGCGGATCAGCAGCAAGCTGGAACAGGAAGCCAACGCCAGCGCCCAGA

CCAAGTGCGACATCGAGATCGGCAACTTCTACATCCGGCAGAACCACGG

CTGCAACCTGACCGTGAAGAACATGTGCAGCGCCGACGCCGACGCCCAG

CTGGATGCTGTGCTGAGCGCCGCCACCGAGACATACAGCGGCCTGACCC

CCGAGCAGAAAGCCTACGTGCCCGCCATGTTCACAGCCGCCCTGAACAT

CCAGACATCTGTGAATACCGTGGTCCGCGACTTCGAGAACTACGTGAAG

CAGACCTGCAACAGCAGCGCCGTGGTGGACAACAAGCTGAAGATCCAGA

ACGTGATCATCGACGAGTGCTACGGCGCTCCCGGCAGCCCCACCAACCT

GGAGTTCATCAACACCGGCAGCAGCAAGGGCAACTGCGCCATCAAGGCC

CTGATGCAGCTGACCACCAAGGCCACCACCCAGATCGCCCCCAAACAGG

TGGCCGGCACCGGCGTGCAGTTCTACCACCACCACCATCACCACGAGCA

GAAGCTGATCAGCGAAGAGGACCTGCACCATCATCACCATCACGATGAG

CTGTGAAAGCTTTTAATTAAGAATTCGAGCTC

SEQ ID NO: 18 is a 478 bp nucleic acid sequence
encoding the Pg3.2 protein (148 aa):
CCATGGGTAGGCTTAACCAGTGCATGTCTGCTAACGAGGCTGCTATT

ACTGATGCTGCTGTTGCTGTTGCTGCTGCATCTAGCACTCATAGGAAGG

TGGCATCTTCTACCACCCAGTACGATCACAAAGAGAGCTGCAACGGTCT

GTACTACCAGGGATCTTGCTACATCCTGCACAGCGATTACCAGCTGTTC

-continued
TCCGATGCTAAGGCTAACTGCACTGCTGAGTCCTCTACCCTGCCTAACA

AGTCTGATGTGCTTATCACCTGGCTGATCGATTACGTTGAGGATACCTG

GGGTTCCGATGGTAACCCTATTACCAAGACCACCTCCGATTACCAGGAT

TCCGATGTGTCTCAAGAGGTGAGGAAGTACTTCTGCGTTAAGACCATGA

ACGAGCAGAAGCTGATCAGCGAAGAGGATCTTCATCACCATCACCACCA

CGATGAGCTGTAGAAGCTTTTAATTAAGAATTCGAGCTC

SEQ ID NO: 19 is a 496 bp nucleic acid sequence
encoding the Pg3.1 protein (154 aa):
CCATGGGCCGGCTGAACCAGTGCATGAGCGCCAACGAGGCCGCCATC

ACAGATGCCGCCGTGGCCGTGGCCGCTGCCAGCAGCACACACAGAAAGG

TGGCCAGCTCCACCACCCAGTACGACCACAAAGAGAGCTGCAACGGCCT

GTACTACCAGGGCAGCTGCTACATCCTGCACAGCGACTACCAGCTGTTC

AGCGACGCCAAGGCCAACTGCACCGCCGAGAGCAGCACCCTGCCCAACA

AGAGCGACGTGCTGATCACCTGGCTGATCGACTACGTGGAAGATACCTG

GGGCAGCGACGGCAACCCCATCACCAAGACCACCAGCGATTACCAGGAC

AGCGACGTGTCCCAGGAAGTGCGGAAGTACTTCTGCGTGAAAACCATGA

ACCACCACCACCATCACCACGAGCAGAAGCTGATCAGCGAAGAGGACCT

GCACCATCATCACCATCACGATGAGCTGTGAAAGCTTTTAATTAAGAAT

TCGAGCTC

Example 2

Transformation Vectors

Nucleic acid sequences encoding the PG1, PG2 and/or PG3 antigenic proteins were assembled into the intermediate vectors PMA or PMA-T available at GenArt Life Technologies (FIG. 1A). Referring to this figure, the synthetic cDNA fragments Pg1.2 (top) 3236 base pairs, Pg2.2 (middle) 3007 base pairs, and Pg3.2 (bottom), 2846 base pairs were assembled from the synthetic oligonucleotides and/or PCR products. In the name of the plasmid 11ABCIZC-Pg12-PMA-T, "11ABCIZC" refers to the Quality Assurance Information provided for each synthetic plasmid product by the company, "Pg12" refers to synthetic polynucleotides Pg1.2 and "PMA-T"

Pnos promoter and Tnos terminator, and multiple cloning sites NcoI-SacI, NcoI-HindIII, and NcoI-EcoRI.

A binary vector harboring an expression cassette including polynucleotide sequences Pg1 (B5) and Pg2 (L1) and/or Pg3 (A33) driven by the CaMV-35S promoter was also engineered using the pBIN-based vector, pB002 (Golovkin et al. 2003 Proc Natl Acad Sci USA 100: 10558-10663, which is incorporated herein as if fully set forth). The vector contains bar gene for selection of transgenic plants in PPT supplemented medium. Plasmid pB002-37B5 was introduced into Agrobacterium. tumefaciens for use in collard transformation. The pBINPLUS-based binary vector containing the nptII gene for kanamycin selection was used for tobacco, tomato, carrot and collard transformation. The plasmids were introduced into A. tumefaciens by electroporation.

For stable transformation, expression cassettes were introduced into the disarmed A. tumefaciens strain LBA4404. For transient expression system, expression cassettes were introduced into Agrobacterium strain GV3101. Agrobacterium was grown overnight in LB medium supplemented with appropriate antibiotics at 28° C. Bacterial dilutions were applied for plant transformation.

Example 3

Plant Transformation

Generation of Transgenic Plants.

Tobacco, tomato, carrot and collard explants were transformed with constructs encoding immunogenic proteins. Transgenic lines were selected and tested by PCR and Western blotting for the presence of L1, B5 and A33 proteins.

Stable Transformation.

Stable transformation was performed as described in Pogrebnyak et al. 2006 Plant Sci. 171: 677; Pogrebnyak et al. 2005 Proc Natl Acad Sci USA 102: 9062; Golovkin et al. 2007 Proc Natl Acad Sci USA 104: 6864, all of which are incorporated herein by reference as if fully set forth.

Transient Expression.

"Magnifection" a transient production system was used for rapid expression of antigens in plants. Proteins were readily detected in the extracts of transfected leaves when expression was targeted to the apoplast area.

Electro-competent Agrobacterium cells were prepared in LB medium supplemented with 50 µg/ml rifampicin as overnight bacterial culture. The pelleted culture was washed twice with ice-cold sterile 10% glycerol and resuspended in 10 ml 10% glycerol to make 25 µl aliquots frozen in liquid nitrogen and stored at −80° C. For electroporation, 1 µl (0.1 µg) of plasmid DNA (Qiagen miniprep) was mixed with 25 µl electrocompetent Agrobacterium cells strain GV3101 in LB medium supplemented with 25-50 µg/ml gentamycin, 10 µg/ml rifampicin and electroporated. Following electroporation, samples were incubated in 1 ml LB for at least 2-3 hours at 28° C. and at 120 rpm. The bacterial cells were plated onto selection LB media and incubated for 2-3 days at 28° C. Glycerol stocks for further use were prepared as 1:1 mix of 30% sterile glycerol with fresh overnight bacterial culture and stored at −80° C.

The "deconstructed" tobamovirus replicon magnICON system that was used for transformation was provided by Icon Genetics GmbH as described in Gleba et al. 2005 Vaccine 23: 2042, Marillonnet et al. 2005 Nat Biotechnol 23: 718; Marillonnet et al. 2004 Proc Natl Acad Sci USA 101: 6852, all of which are incorporated herein by reference as if fully set forth. Six-nine weeks old N. benthamiana plants were routinely transformed with the fresh overnight three-component cultures prepared from glycerol stocks in selective LB media incubated at 28° C. for 24 hours and mixed in equal proportions immediately prior the transformation experiments. One component (Agrobacterium cells) carried genes encoding the PG1, PG2, PG3 variants subcloned into the pICH11599 vector. The expression cassettes that included genes of interest were subcloned into the pICH11599 within the polylinker for NcoI-SacI, or NcoI-HindIII, or NcoI-EcoRI restriction sites. The other two components included the pre-manufactured vectors carrying either the targeting signal (cytosolic pICH10570) and the pICH10881 carrying the integrase as described in Giritch et al. 2006 Proc Natl Acad Sci USA 103(40): 1470, which is incorporated herein by reference as if fully set forth. The synthetic coding sequences were sub-cloned from the plasmid DNA supplied by synthesis facility Geneart (Life Technologies) and Genescript USA. The pICH11599 constructs were given the names of the corresponding sequences encoding antigenic proteins such as Pg1, Pg2, Pg3 or consecutive Pg numbers. All genes of interest included the ATG start codon within the 5' NcoI site. An additional amino acid could be added at the N-terminal end of the expressed protein. In constructs designed for expression in cytosol (pICH10570), the protein was expressed from the first ATG of the cloned gene. All plasmids had a carbinicillin/ampicillin resistance gene for propagation in bacteria. Three vector-based components were mixed and diluted at least ten times with the Infiltration Buffer (IB) (10 mM MES-NaOH; pH 5,5;10 mM $MgSO_4$).

Production and Purification of Pg1 and Pg2 (Pg3) Recombinant proteins from Plant Tissues.

Purification was facilitated by the presence of conventional c-Myc and His tags. Additionally, an ER retention signal (HDEL) was inserted between the tags and the stop codon. The amino acid sequence composition also included N-terminal signal peptides.

Extraction Protocol for PG1:

a total of 140 g of frozen (at −80° C.) leaf material was harvested at 7-9 days post infiltration (dpi). The tissue was grounded in 700 ml of extraction buffer (50-100 mM Na Phosphate, pH7.7-8.0; 0.3M NaCl; 0.2% Tween-20; 1.5 mM β-Mercaptoethanol; 0.05% Sigma Inhibitors) using Brinkman Polytron Homogenizer at 27,000 rpm. Insoluble parts were pelleted (Beckman) at 9,000 rpm twice for 15 min at 4° C. Approximately 800 ml of the supernatant (with 1.4% TCP content) included approximately 400 µg of PG1 protein. Following the flow-filtering through Miracloth (Calbiochem), the protein was harvested by Ni-sepharose Fast Flow (Amersham Biosciences) resin equilibrated with the extraction buffer. Resin was transferred into 15-25 ml column, washed with the extraction buffer and the elution buffer (EB) supplemented with 20 mM Imidazol. Elution was performed with EB supplemented lwith 20 mM Imidazol in small volumes and dialyzed against the sterile PBST. The collected fractions were ready for the 2-step purification with C-Myc resin. The protein yield was approximately 30 µg and corresponded to 30% recovery.

All the collected fractions were tested individually by Western blot analysis and combined into one fraction. The fraction was concentrated using the 10× (Amicon Ultra) centrifugal Filter device with MWCO either 10K or 5K (Millipore). The fraction was dialyzed against PBS (or PBS/Saline) with 0.01% Tween-20. The purified protein was ready for immunization. The recovery of the recombinant product from biomass 7 dpi was estimated to be approximately 25%.

*Tobacco (Nicotiana tabacum* cv. Wisconsin and LAMD-609)

Tobacco cultivars Wisconsin and LAMD-609 (low nicotine) were used for all experiments. Tobacco seeds were surface sterilized and plated on the solidified MS medium (Murashige and Skoog 1962 Physiol. Plant, 15: 473) supplemented with 1% sucrose, 0.7% agar, pH 5.8. Seeds were germinated in the growth chamber at 24° C., 16/8 h light/dark photoperiod and light intensity of 40 μE/m$^2$/s$^1$. After 2-3 weeks of culturing, seedlings were excised and transferred to the Magenta boxes containing the MS medium supplemented with 0.7% agar and 3% sucrose.

Figure 2A:
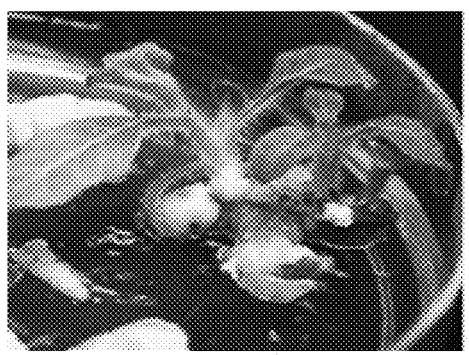
FIGS. 2A-2C illustrate transgenic tobacco events which express antigenic proteins grown in vitro (FIGS. 2A and 2B) and in soil (FIG. 2C).
Figure 2B:
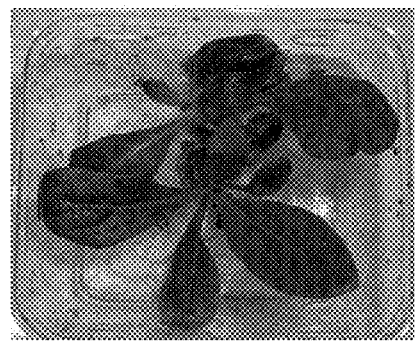
Figure 2C:

The *Agrobacterium* strain LB4404 was used for transformation experiments. Leaves of 5-6 week-old aseptically grown plants were inoculated with the *Agrobacterium* cell suspension. Specifically, leaves were cut into segments 0.5 to 0.7 cm in size and incubated in the *Agrobacterium* suspension at $OD_{600\ nm}$ of 0.5 for 10 min. Leaf segments were blotted dry with the sterile filter paper and plated onto the surface of the solidified MS medium supplemented with 3% sucrose and 0.7% agar in sterile 100 mm Petri dishes, sealed with Parafilm and incubated at 24° C. in the dark. After 2 days of co-cultivation, leaf segments were transferred to the selection/regeneration MS medium supplemented with 3% sucrose, 1 mg/l BAP, 0.1 mg/l NAA, 100 mg/l kanamycin, 300 mg/l timentin, 0.7% agar and incubated at 24° C. and 16/8 h light/dark photoperiod. After 5-6 weeks of selection, the putative transgenic green shoots were formed (FIG. 2A). These shoots were excised and transferred to Magenta boxes containing MS medium supplemented with 100 mg/l kanamycin, 3% sucrose, 0.7% agar and 200 mg/l timentin for rooting. As shown on FIG. 2A, transgenic shoots were developing on the medium supplemented with kanamycin. Control wild type tobacco plants failed to grow under similar conditions. Transgenic shoots were further transferred to Magenta boxes for root induction (FIG. 2B). Plants that rooted in the presence of 100 mg/l kanamycin were tested for expression of recombinant products. The best transgenic lines were chosen for root induction and then were transferred to soil to mature and set seeds (FIG. 2C). Plantlets were gently removed from the agarized media and their roots were gently rinsed with tap water before further transfer into Metro-mix soil. Each plant was grown in 10-15 cm pot covered with glass for the first 3-4 days to keep high humidity. Plants were maintained in the greenhouse at 23° C. to 25° C. and 16/8 day/night period.

Figure 2D:
FIG. 2D illustrates PCR analysis of the transgenic tobacco events.

Transgenic plants were screened by a universal PCR reaction for the integration events based on detection of the nptII gene marker encoding resistance to kanamycin (FIG. 2D). Referring to this figure, all positive transformants (14 from 24 shown in the figure) produced PCR products of expected molecular size of approximately 500 bp with the specific primers: the forward primer 5-'TGAATGAACT-GCAGGACGA-3' (SEQ ID NO: 20) and the reverse primer 5'-AGCCAACGTATGTCCTGAT-3' (SEQ ID NO: 21); following 30 polymerization cycles with annealing temperature 50° C. using Takara polymerase protocol from Clonetech.

Figure 2E:
FIG. 2E illustrates Western blot analysis of the transgenic tobacco events.

Transgenic plants were further screened for the presence of C-Myc tags. In particular, crude total protein extract were tested by SDS-PACE Western blot analysis using the cmyc mAb (ATCC, Manassas) and goat anti-mouse antibody (Ab) (Upstate NY) (FIG. 2E). Referring to this figure, PG1 recombinant product was detected in total soluble protein (TSP) extracts as a single band (~40 kDa) in 7 out from 8 tested TSP samples. It is a known fact that some integration events, random by nature, are silent and do not produce the recombinant product. The correct molecular weights were verified by lkDa kaleidoscope marker (Biorad).

Tomato (*Lycopersicon esculentum*)

Cultivar Money Maker was obtained from the Totally Tomato Company, US. Seeds were sterilized with 70% ethanol and 1.5% sodium hypochlorite solution and plated onto solid MS medium supplemented with 3% sucrose and 0.7% agar in Phytatrays. 50 seeds were plated per each container and germinated in the growth chamber at standard lighting conditions 16/8 hours day/night period and 240° C. Ten-day-old seedlings were used for *Agrobacterium*-mediated transformation with vector pBINPLUS (van Engelen et al. 1995 Transg Res 4: 288) carrying single or double plant expression cassettes with Pg1 and/or Pg2 and driven by CaMV-35S or Ocs-Mas (super) promoters (Ni et al. 1995 Plant J 7: 661). The nopaline synthase (Nos) terminator was used in both cases. Expression cassette also contained plant-specific endoplasmic reticulum retention signal and for purification needs C-terminal c-Myc tags or a histidine tags (Golovkin 2011 Chpt 14, Bioprocess Sci and Techn, Nova). The vector also contained the nptII gene for kanamycin selection of transgenic plants.

For transformation, cotyledons and hypocotyls were cut into 3 mm-5 mm segments and incubated in *Agrobacterium* suspension at $OD_{600\ nm}$ 0.3 for 10 minutes. Following incubation, explants were blotted dry with sterile filter paper and plated onto the solid MS medium supplemented with 3% sucrose, 0.7% agar and 5004 of acetosyringone in Petri dishes. Dishes were sealed with parafilm and incubated for 2 days at 24° C. in the dark.

After two days, explants were transferred to MS recovery medium supplemented with 3% sucrose, 0.7% agar, 1 mg/l zeatin and 300 mg/l timentin. After incubation for one week, explants were transferred to selection/regeneration MS medium containing 3% sucrose, 0.7% agar, 2 mg/l zeatin, 70 mg/l kanamycin and 300 mg/l timentin.

Figure 3A:
FIGS. 3A-3B illustrate in vitro selection and regeneration of transgenic tomato events.
Figure 3B:

After 5-6 weeks of culturing, formation of the green shoots on the plated explants was observed (FIG. 3A). It was further noticed that cotyledons explants exhibited higher regeneration capacity than hypocotyls and on average produced more green kanamycin-resistant shoots. Shoots that reached at least 1 cm in height were transferred on root induction MS medium supplemented with 3% sucrose, 0.7% agar, 100 mg/l kanamycin, 300 mg/l timentin and 2 mg/l indolebutyric acid (IBA). After 1-2 weeks of cultivation, putative transgenic shoots initiated rooting on this medium. Well developed rooted shoots were used for further analyses (FIG. 3B)

Figure 3C:
FIG. 3C illustrates the transgenic tomato event grown in soil.

After transformation and selection, 20 putative transgenic lines were transferred to greenhouse conditions to set fruits and were used for further evaluation (FIG. 3C).

Carrot (*Daucus carota*)

Carrot seeds cultivar Thumbelina were surface sterilized with sodium hypochlorite as described and transferred to MS medium supplemented with 3% sucrose and 0.7% agar. Twenty seeds were plated in Petri dishes and cultivated at 24° C. and 16 h-light/8 h-dark photoperiods. Plants were transformed with *Agrobacterium tumefaciens* strain LBA4404 harboring pBINPLUS vector containing one or two expression cassettes with Pg1, Pg 1 and/or Pg3 sequences.

Figure 4A:
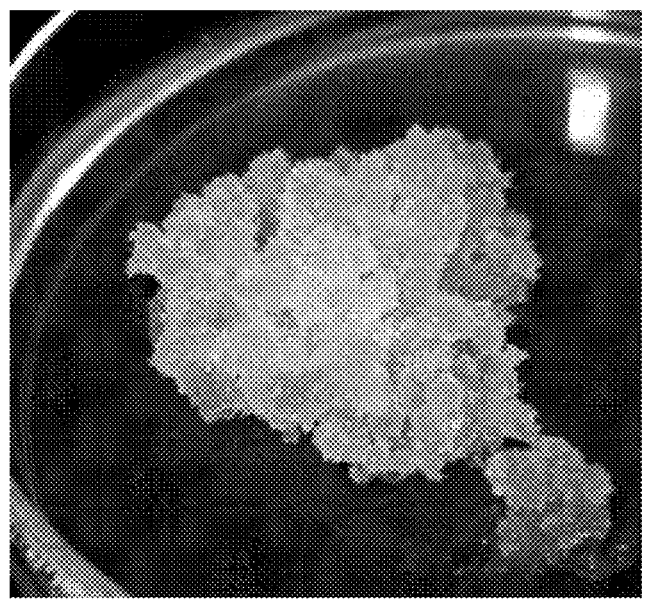
FIG. 4A illustrates production of a transgenic carrot callus.

Briefly, for generating transgenic cell lines the hypocotyls of two-week-old plants were cut into 1 cm pieces and inoculated with the suspension of *Agrobacterium tumefaciens* strain LBA4404 ($OD_{600}$-0.3) for 10 min, following with co-cultivation on MS medium supplemented with 100 μM acetosyringone for 2 days at 23° C. For callus induction, the explants were transferred onto MS medium supplemented with 0.5 mg/l NAA, 0.3 mg/l BAP, 1 mg/l 2.4-D and 300 mg/l timentin and incubated in the dark at 24° C. for at least 2 weeks. Explants were further transferred onto selection MS medium supplemented with 0.3 mg/l NAA, 0.2 mg/l BAP, 2 mg/l 2.4-D, 300 mg/l timentin and 100 mg/l kanamycin. After 5-6 weeks of selection, putative transgenic callus tissues were produced on the selection medium, sub-cultured and maintained in the dark. Kanamycin-resistant callus was passaged every 4-5 weeks. Individual clones of kanamycin-resistant transgenic calli were obtained with expression cassettes (FIG. 4A).

Figure 4B:
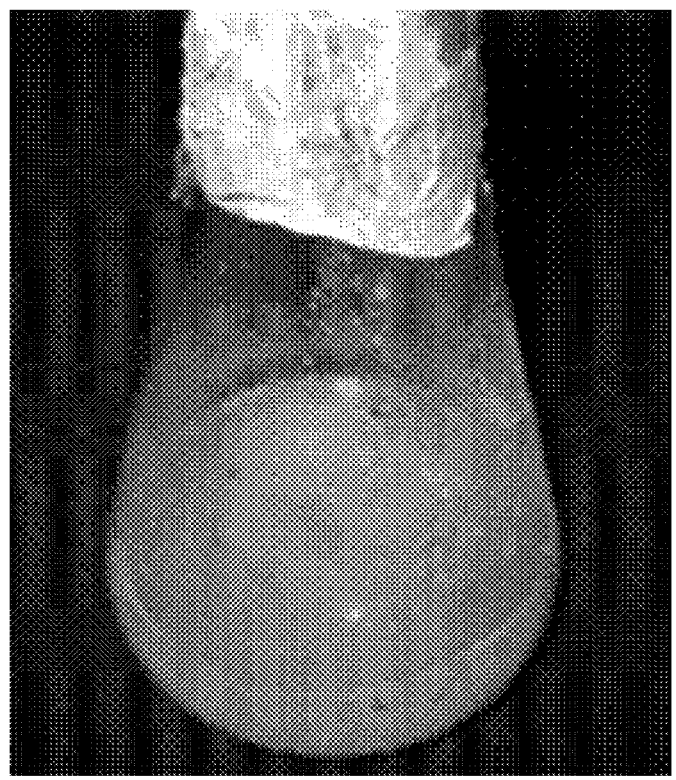
FIG. 4B illustrates the cell suspension generated from the transgenic carrot callus.

Carrot cell suspensions suitable for plant type bioreactor production were initiated from transgenic calli using liquid MS medium supplemented with 1 mg/l 2.4-D. (FIG. 4B). For this, approximately 1 g of fresh weight callus tissue was transferred into 50 ml of liquid MS medium and plated into sterile 250 ml conical flasks. Cell cultures were incubated on a rotary shaker at 150 rpm and maintained in the dark at 25° C. Further maintenance, stabilization and biomass collection of cell suspensions were carried out in MS medium with 2.4-D at 18-20 day intervals. Transgenic carrot cell suspension lines were confirmed for the presence of recombinant antigens PG1, PG2 and PG3 by Western blot analysis.

Once confirmed as useful source of recombinant target protein expressers, calli were induced to regenerate whole plants by embryogenesis. For this, callus tissues were placed on the MS callus induction medium supplemented with 1 mg/l 2.4-D, 100 mg/l kanamycin and 300 mg/l timentin for 3-4 months. Callus tissues were maintained on this medium for 4- to 5-week intervals and then transferred to the hormone-free MS medium supplemented with 100 mg/l kanamycin and 300 mg/l timentin. Small embryos were formed from the callus and further developed into mature carrot plants. Selection of transgenic plants was performed using kanamycin.

Collard (*Brassica oleracea* var *acephala*)

Cultivars Morris Heading, Vates and Georgia were obtained from the Carolina Seeds Co., Hartford, Conn.). Seeds of collard may be sterilized in 70% ethanol for 1 min followed by 2% sodium hypochlorite for 20 min. After rinsing three times in sterile distilled water, seeds were placed in germination medium MS-1 containing MS macro- and microelements 1% sucrose and 0.8% agar. Germination and in vitro culture was carried out at 24° C. at 16 h-light/8 h-dark photoperiods with light intensity of 40 mE/m2/S1. Cotyledons and hypocotyls of collard plants were cut from 4-, 7- and 10-dayold seedlings and placed on MSR-I regeneration medium. Explants were cultured for 5 weeks and tested for shoot regeneration efficiency.

For collard transformation, vaccinia virus sequences Pg1, Pg2 and Pg3 were arranged in single or double cassette form and introduced either in the pBINPLUS vector containing the nptII gene conferring resistance to kanamycin or in pB002 containing the bar gene conferring resistance to phosphinothricin (PPT). Transgenes were driven by the CaMV-35S or Ocs-Mas (super) promoters (Ni et al. 1995). The nopaline synthase (Nos) terminator was used in all constructs.

Transformation with pB002:

Four-day-old cotyledon and hypocotyl explants were inoculated with *Agrobacterium* suspension for 10 min. After blotting dry with sterile filter paper, explants were transferred to MS-2 co-cultivation medium supplemented with acetosyringone and incubated in the dark for 2 or 3 days at 240° C.

After co-cultivation explants were transferred to MS-3 regeneration medium without selection for 0-12 days and then transferred to MS-5 regeneration selection medium containing PPT (Sigma, St. Louis, Mo.). After 4-5 weeks of selection, regenerated green shoots (putative transformants) were formed. Green shoots were excised and transferred to MS-7 selection medium supplemented with increased concentration of selection agent, e.g., PPT, for rooting. Selected plantlets with roots were transferred to soil. The transgenic status of the plants was confirmed by PCR. For seed production, collard plants were placed in a cold room (40° C.) for 1 month and then transferred to a plant growth chamber (240° C.). Transgenic plants were self-pollinated for production of T1 seeds.

Transformation with pBINPLUS.

Figure 5A:
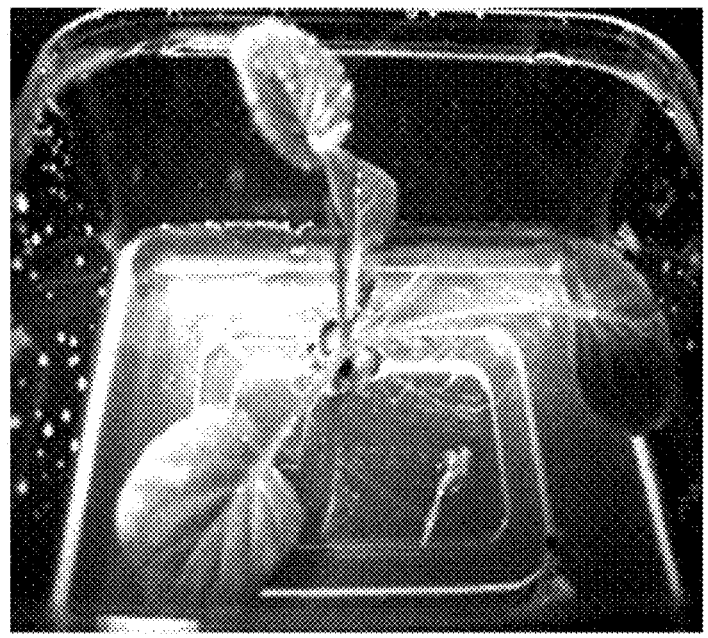
FIG. 5A illustrates the transgenic collard plant grown in vitro.
Figure 5B:
FIG. 5B illustrates the transgenic collard plant grown in soil.

For transformation experiments, four-day-old cotyledon and hypocotyl explants were inoculated with *Agrobacterium* suspension at $OD_{600\,nm}$ 0.1 for 10 min. After blotting dry with sterile filter paper, explants were transferred to the co-cultivation MS medium supplemented with 100 μM acetosyringone and incubated in the dark for 2 days at 24° C. After co-cultivation, explants were transferred to the regeneration medium without selection (MS supplemented with 20 μM AgNO3, 1 mg/l BAP, 1 mg/l zeatin, 0.1 mg/l NAA and 300 mg/l timentin). After 8 days, explants were transferred to the selection medium (MS supplemented with 20 μM AgNO3, 1 mg/l BAP, 1 mg/l zeatin, 0.1 mg/l NAA, 300 mg/l timentin and 30 mg/l kanamycin. After 4-5 weeks on selection medium, putatively transformed green shoots were formed. It was observed that the cotyledon explants produced twice more putative transgenic shoots compare to the hypocotyl explants. Healthy green shoots (1-2 cm) were excised and transferred to the MS medium supplemented with 3% sucrose, 0.8% agar, 300 mg/l timentin and 50 mg/l kanamycin for rooting. Under the selection conditions, transgenic shoots showed good growth and development of roots in comparison to the non-transgenic shoots that did not grow or root and eventually died. FIG. 5A illustrates growth and rooting of the transgenic shoot in the Magenta box. Rooted plantlets 4-5 cm in height were transferred to soil (Metromix; K. C. Schoefer, York, Pa.) for further growth in the greenhouse (FIG. 5B). It was observed that transgenic collard plants were growing fast in the greenhouse and produced a large amount of leaf tissues in 2.5-3 months. For example, three month-old collard plant produced 0.5 kg of biomass. A total of 16 transgenic collard lines were produced after transformation experiments.

For seed production, collard plants were placed in a cold room (4° C.) for a month and then transferred to a plant growth chamber (24° C.). Transgenic plants were tested for the presence of nptII selection marker and c-Myc tags as detected by immunological testing (similar to analyses shown in FIGS. 2D-2E). Transgenic collard plants were also tested for with the expression of antigens against small pox. The high expressors then were grown up for self-pollination to produce T1-generation seeds.

Example 4

Expression of PG1 (B5), PG2 (L1) and PG3 (A33), Immunogenic Proteins in Plants

Figure 6A:
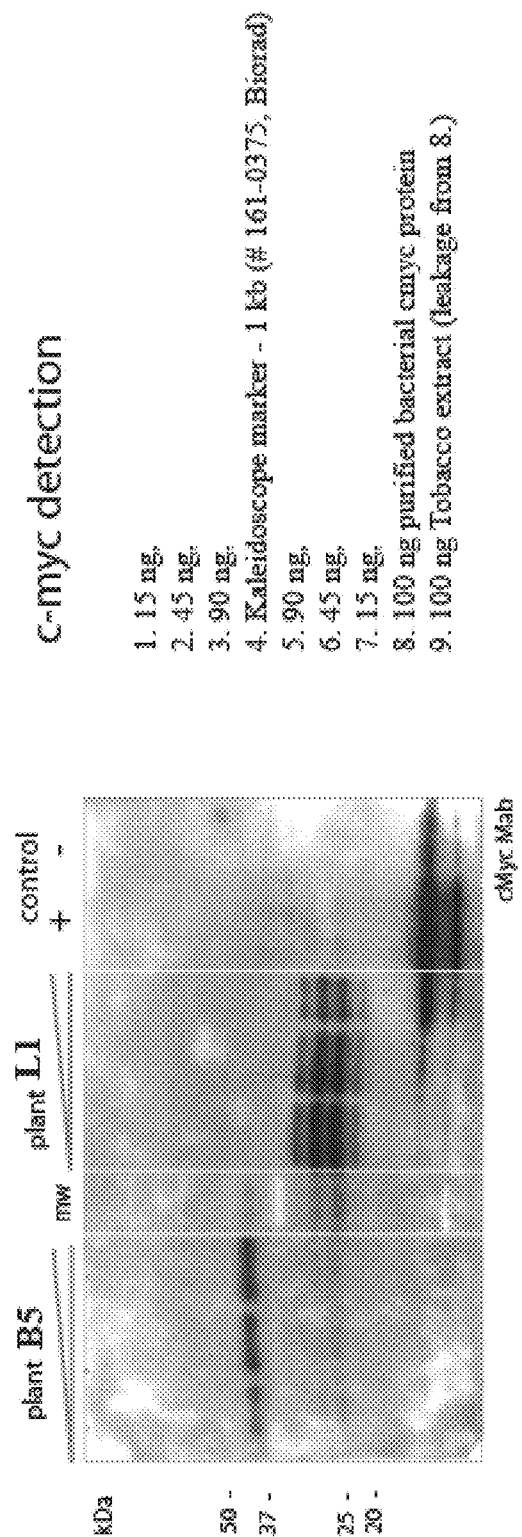
FIG. 6A illustrates Western blot analysis of transgenic tobacco plants expressing plant B5 (PG1) and plant L1 (PG2) proteins detected by c-Myc—specific monoclonal antibody (mAb).
Figure 6B:
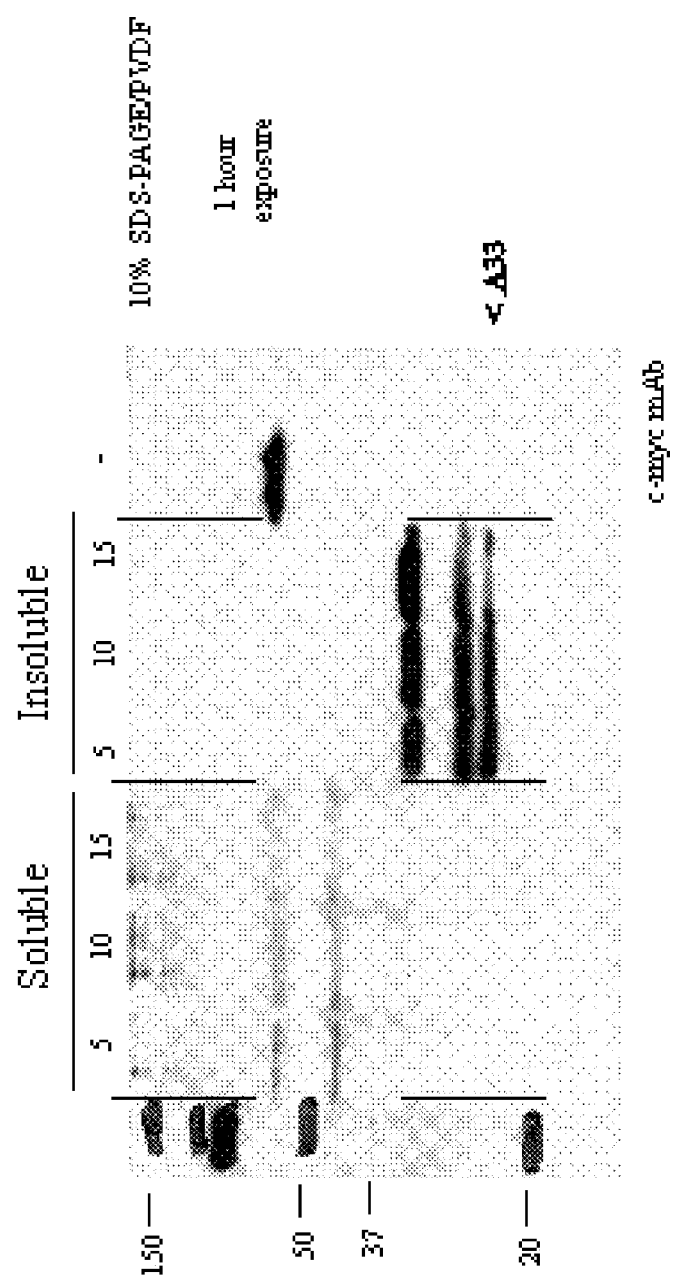
FIG. 6B illustrates Western blot analysis of a transgenic tobacco plant expressing the partially soluble plant A33 (PG3) protein detected by c-Myc—specific monoclonal antibody (mAb).

Smallpox vaccine-candidates L1, B5 and A33 immunogenic proteins, from Vaccinia virus were optimized for successful expression in plants. Stable and transient expression systems for plant transformation were tested. Selected transgenic tobacco plants were analyzed by Western blot using c-Myc-specific mAb. c-Myc mAb were used at 1:5000 dilution factor (ATCC, Mannasssas Va.). Secondary Ab goat anti-mouse (Upstate NY) was used at 1:2500 or even lower dilution to reduce background. Detection was performed using Pierce Super Signal West kit #34080. FIG. 6A demonstrates a combined detection of the plant-derived recombinant products for plant PG1 (plant B5), three consecutive lanes on the left panel, and PG2 (plant L1), three consecutive lanes on the right medium panel. Panels are separated by a lane with 1 kDa molecular weight (mw) Kaleidoscope marker from Biorad. Control panel has a positive (+) C-Myc control (first lane), a commercial bacterial protein, and negative (−) lane loaded with non-transgenic TSP. A detectable leakage of low molecular weight c-Myc occurred into this lane. FIG. 6B illustrates detection of PG3 (plant A33) protein by SDS-PAGE analysis. Plant A33 recombinant product was extracted from lyophilized plant tissues either in the presence of soluble buffer (0.1M Na phosphate pH7.2, 0.3M NaCl, 3% Glycerol, 0.1 mM EDTA, 5 mM β-ME and Sigma inhibitors at 0.05%), concentrated and brought to Laemly loading buffer at the same volume (200 ml) as the insoluble part (pellet) dissolved in Laemly directly. Samples were loaded at increasing concentrations as 5, 10 and 15 ml per lane following the heating at 65° C. for 10 min; first lane is a molecular weight marker (Biorad) and negative control (−) is a commercial c-Myc protein (~50 kDa). Lower dilution of secondary antibodies (1:14000) was compensated by longer film exposure, 1 hour.

Figures 7A, 7B:
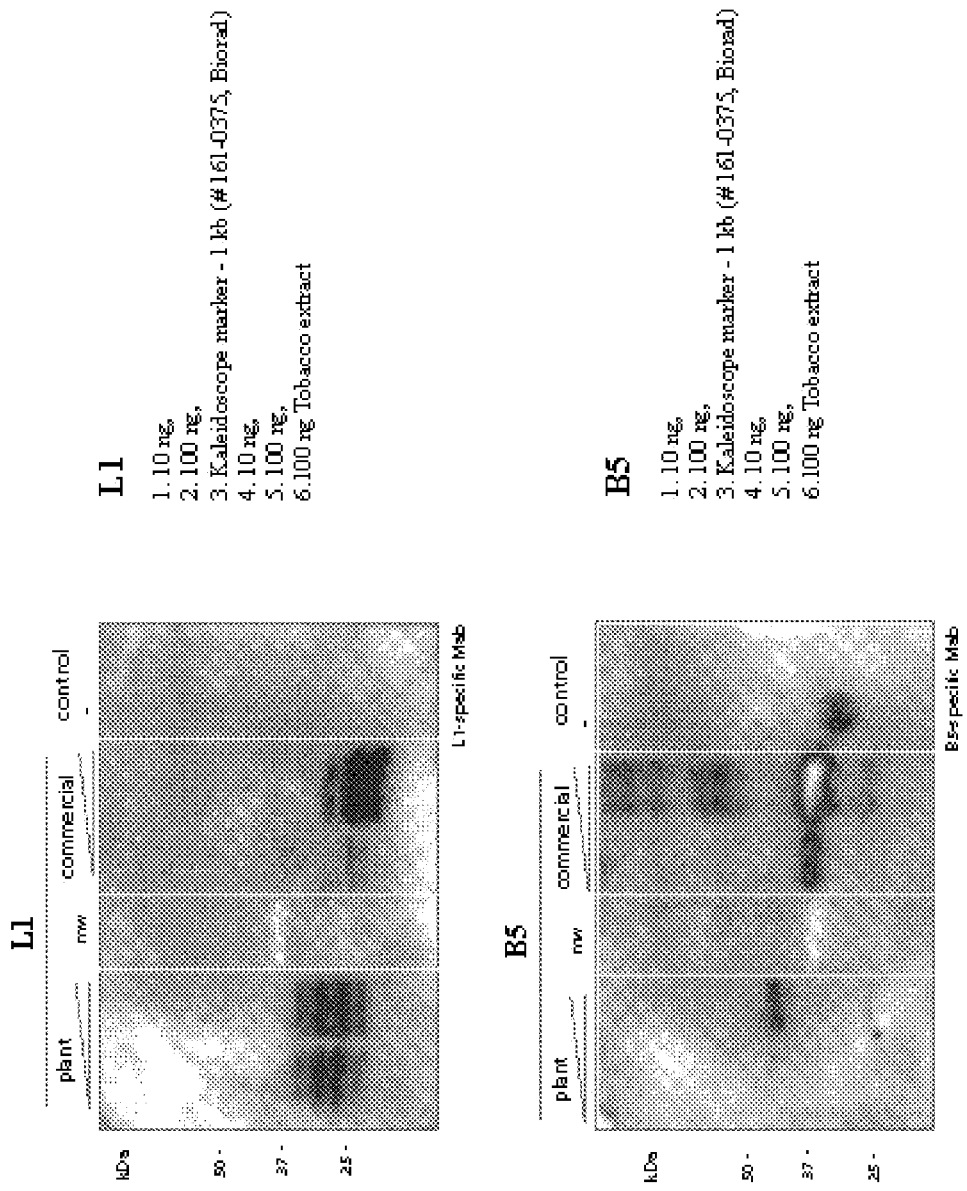
FIGS. 7A-7B illustrate side-by-side Western blot analysis comparing the plant-derived antigenic L1 (PG2) protein (FIG. 7A) and B5 (PG1) protein (FIG. 7B) with commercial products.

FIGS. 7A and 7B illustrate the results of antigen-specific Western blot expression of recombinant antigenic products B5 and L1 obtained from the plants (left panel with two lanes) in side-by-side comparison with the commercial protein (right panel with two lanes) separated by the lane loaded with molecular weight marker (mw); negative control in lane 6 is a non-transgenic plant TSP. Absolute concentrations per lane are given in the figure. Detection was performed using Pierce Super Signal West kit No. 34080. The antigen-specific primary antibodies NR-417 for L1 and NR-433 for B5, as well as the commercial protein samples (e.g., NR2625 for L1, NR546 for B5) were obtained from the specialized BEI resources (http://www.beiresources.org/).

Figure 8A:
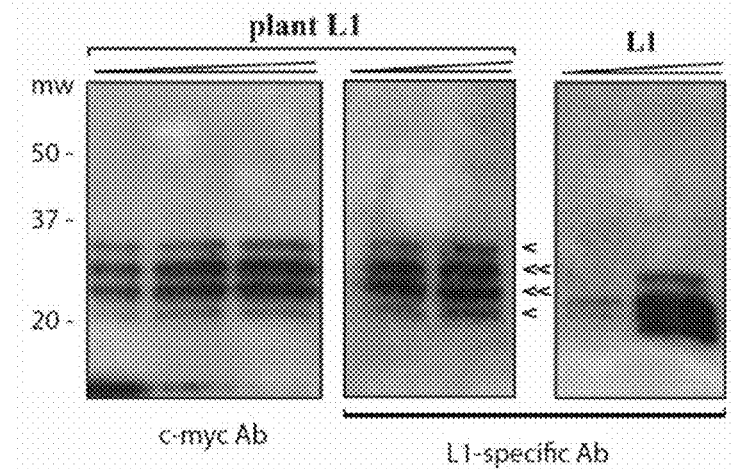
FIG. 8A illustrates the plant L1 prepared and detected by c-Myc and L1-specific antibodies (pL1, left and middle panel), and the commercial L1 protein detected by L1-specific antibody (right panel)
Figure 8B:
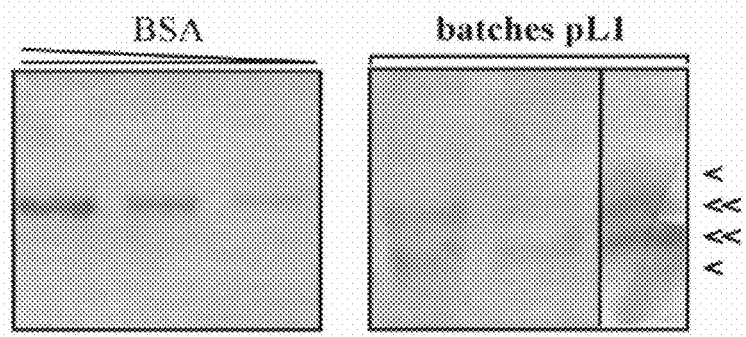
FIG. 8B illustrates Coomassie analysis of the plant L1 protein (right panel) in comparison to a BSA molecular weight standards (left panel).
Figure 8C:
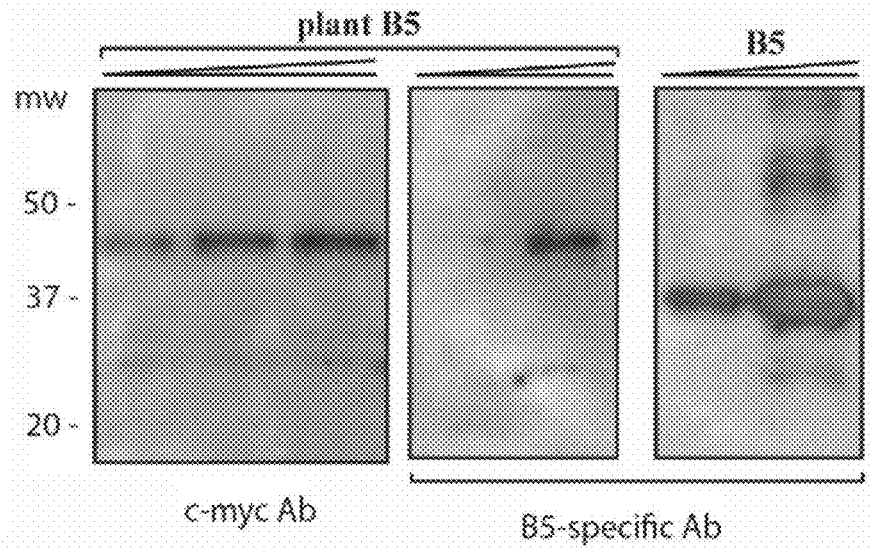
FIG. 8C illustrates the three panel analysis for plant B5 (PG1) protein similar to the analysis performed for plant L1 shown in FIG. 8A.

FIGS. 8A-8C illustrates Western blot expression analysis of recombinant protein production and purification. Western blot was performed using c-Myc- and antigen-specific antibodies. Referring to FIG. 8A, two panels were prepared for pL1 (left panel with three lanes and middle panel with two lanes) and detected by c-Myc- and L1-specific antibodies as compared to commercial L1 product (right panel with two lanes) detected with specific Ab. In the panels, uneven loading was intentional. Multiple forms of pL1 were expected and indicated by arrowheads. Evaluation of the protein expression was based on the fact that recombinant plant L1 can be detected by both mAbs (c-Myc tag incorporated in the synthetic form) but commercial preparations cannot be detected using these antibodies. FIG. 8B shows visual quantification by Coomassie analysis performed for pL1 (right panel). Referring to this figure, three lanes were loaded with pL1 pre-operational batches as volume aliquots (1/20) in comparison to standard BSA (Sigma) molecular weight standard (left panel). Lanes were loaded at 5× molecular weight increments). Expected multiple forms of pL1 are indicated by arrowheads.

FIG. 8C illustrates the three panel analysis for pB5, the initially produced recombinant product, presented here for comparison to pL1 (See explanations for FIG. 8A).

Figure 9A:
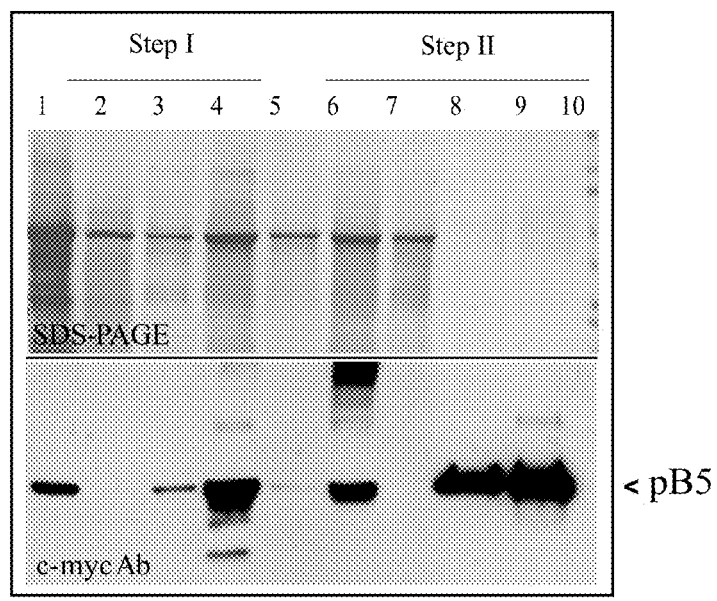
FIG. 9A illustrates the major purification steps of the soluble form of plant B5 protein visualized by SDS-PAGE staining (upper panel) and Western blot analysis with c-Myc mAb (lower panel).
Figure 9B:
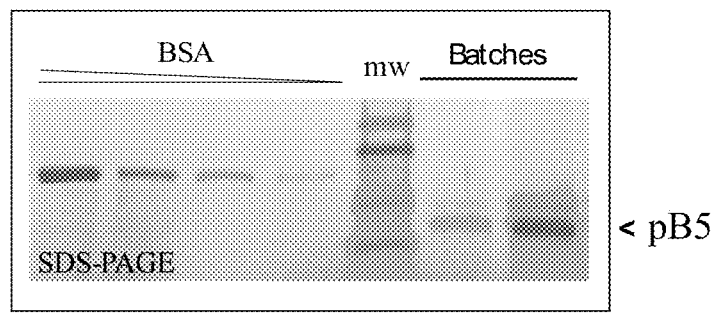
FIG. 9B illustrates data of visual evaluation analysis of concentrated recombinant pB5 originated from separate purified batches compared against a standard bovine serum albumin (BSA) titration curve.
Figure 9C:
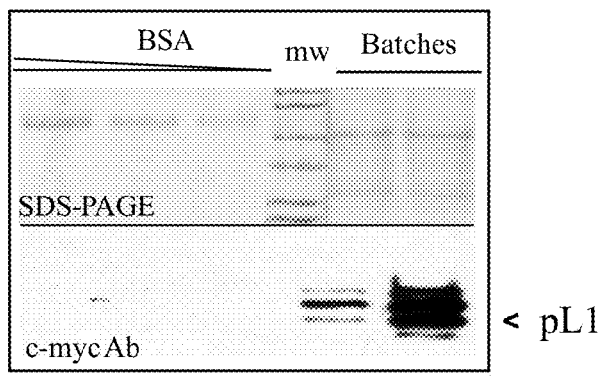
FIGS. 9C-9D illustrate data on expression and purification of plant L1 protein (FIG. 9C) and plant A33 protein (FIG. 9D) using the steps identified with respect to FIG. 9A.
Figure 9D:
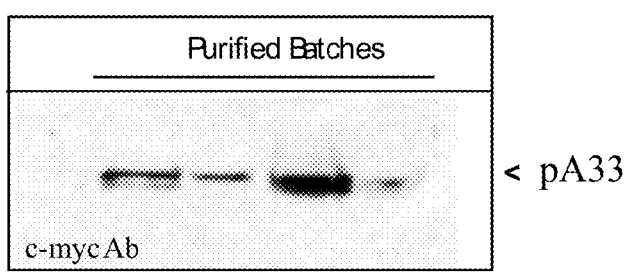

Soluble B5, L1 and A33 proteins expressed transiently in tobacco plants (designated plant-derived B5, L1, and A33 or pB5, pL1 and pA33) were extracted. Powdered material was used in a two-step affinity purification (Ni- and c-Myc mAb affinity columns) to obtain standardized samples with more than 50% purity (FIGS. 9A-9D). It was observed that L1, B5 and A33 immunogenic proteins remained stable in lyophilized plant tissues for several months at 100 mg/kg level when stored in air-tight containers at ambient temperatures or 4° C. FIG. 9A illustrates the major purification steps of the soluble form of pB5 protein visualized by SDS-PAGE staining (upper panel) and Western blot analysis with c-Myc mAb (lower panel). pB5 in a total soluble protein (TSP) extract was detected as a single band (lane 1). Lanes 2-5 represent consecutive metal affinity Ni-column elutions (Step I), and lanes 6-9 represent fractions eluted from the c-Myc-mAb-affinity column (Step II). The lanes include the following elutions: lane 1, TSP extract; lane 2, extract washed with 5 mM imidazole; lane 3, extract washed with 20 mM imidazole; lane 4, elution in 80 mM imidazole; lane 5, consequent elution in 120 mM imidazole; lane 6, dialyses of eluate for c-Myc-mAb-affinity column application (c-Myc-column); lane 7, flow-through in PBS buffer; lane 8, elution with c-Myc peptide; lane 9, consequent elution in acid glycine buffer (pH 2.5). FIG. 9B shows data of visual evaluation analysis of concentrated recombinant pB5 originated from separate purified batches compared against a standard bovine serum albumin (BSA) titration curve. In FIG. 9B, right lanes are loaded with sample aliquots of purified batches (batches) and compared to standard BSA (Sigma) loaded at 5× increments. Panels are separated by a lane with molecular weight marker (mw). The main pB5 product band (~40 kDa) is indicated by arrowheads. The estimates were further verified with functional in vivo analysis against the commercial samples. This approach was applied in the initial small-scale test to express vaccinia virus (strain WR) antigenic proteins pL1 and pA33 (FIGS. 9C and 9D). FIG. 9C illustrates data of quantitative evaluation analysis for recombinant pL1 (top panel, explained in 9B) and the corresponding Western blot analysis using c-Myc antibodies (bottom panel). The pL1 major band(s) are indicated by arrowhead. FIG. 9D illustrates Western blot analysis of partially soluble pA33 double step purification batches, yielding a single band product detected by c-Myc antibodies as indicated by arrowhead.

The overall yields were reaching 0.5-2% of the total soluble protein (TSP) and allowed us to purify for up to 100 μg of protein from grams of lyophilized plant tissue.

Example 5

Immunological Assessment of Plant-Produced Antigens in Mice

Purified preparation of plant-derived recombinant protein B5 (pB5) was used to immunize six- to eight-week-old female BALB/c mice (5 or 10 mice per group) by various routes. Plant-derived L1 (pL1) protein was purified according to the same protocol.

Blood and fecal matter were collected from mice 10 days after each immunization. Proteins from fecal pellets were extracted in PBS (10 vol/wt) supplemented with 1% BSA and protease inhibitors. Mice were sacrificed 10 days after the last immunization and bled by cardiac puncture, and sera were analyzed for the presence of antigen-specific antibodies.

Figure 10A:
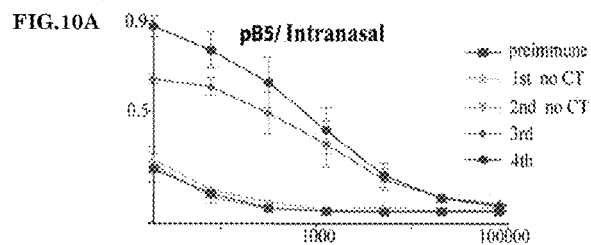
FIG. 10A illustrates the B5-specific immune response in mice after intranasal (i.n.) application of purified plant B5 protein alone (1st and 2nd lines) and together with CT adjuvant (3rd and 4th lines).
Figure 10B:
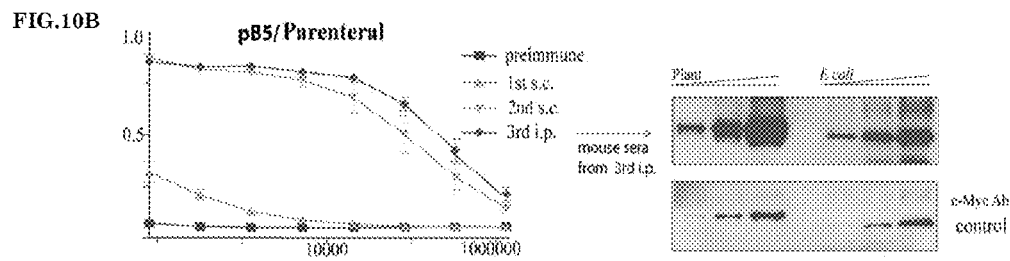
FIG. 10B illustrates the B5-specific antibody response in mice after parenteral immunization (injection) with purified plant B5 protein applied with Freund's adjuvant (left panel) and results of Western blot analysis of sera from mice immunized intraperitonealy (3rd i.p. sample in panel C) (right panel).
Figure 10C:
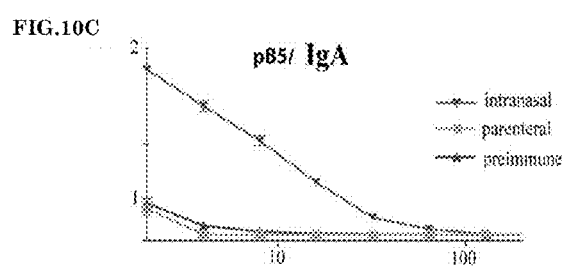
FIG. 10C illustrates the B5-specific IgA response in bronchoalveolar lavage (BAL) from mice after the third mucosal immunization with pB5 protein.
Figure 10D:
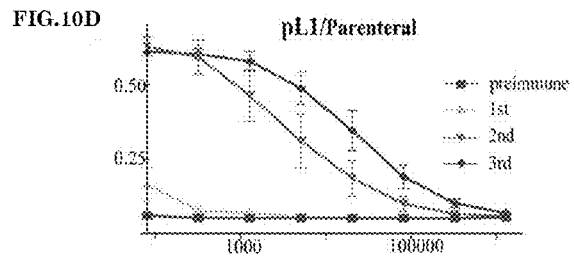
FIG. 10D illustrates the L1-specific antibody response in mice after intramuscular (i.m.) immunization with purified plant L1 protein applied with alum/CpG adjuvant.

Sera from mice immunized intranasally, or parenterally with pB5 were tested for the presence of B5-specific antibodies by ELISA and Western (FIGS. 10A-10C). An antibody response in mice to various routes of administering of antigenic pB5 and pL1 was examined. FIG. 10A illustrates the antigen-specific immune response to pB5 after the intranasal application of the purified plant-derived product without "golden" standard mucosal adjuvant CT (Pt and 2nd lines) and the $3^{rd}$, $4^{th}$ elevated (positive response) lines for pB5 when administered together with CT adjuvant. Referring to this figure, it was observed that intranasal immunization with purified pB5 without any adjuvant did not produce antibodies in mice, although when supplemented with CT led to a distinct anti-B5 immune response. Preimmune line in the graphs corresponds to a negative control.

FIG. 10B illustrates the antigen-specific response after parenteral immunization (subcutaneous (s.c) and intraperitoneal (i.p.) type of injections) with pB5 together with Freund's adjuvant. Corresponding results were verified by Western blot analysis (right panel) that consists of two identical blots detected either by sera from mice immunized intraperitonealy (3rd i.p. sample line in graph) and c-Myc antibodies (c-Myc mAb or Ab) as detection control. Blot has an incremental concentration of TSP extracts from transgenic plants (left three lanes) and a bacterial *E. coli* (right three lanes) recombinant B5 carrying c-Myc tag, all separated by an empty lane. The difference in mobility of B5 protein expressed in a plant and B5 protein expressed in cells of *Escherichia coli* is probably due to the differences in posttranslational modifications in eukaryotes, e.g., glycosylation of pB5. Referring to FIG. 10B, the B5-specific antibody response was observed after parenteral immunization (injection) with purified pB5 protein applied with Freund's adjuvant (left panel) and results of Western blot analysis of sera from mice immunized intraperitonealy ($3^{rd}$ i.p. sample in panel C) (right panel).

The strongest anti-B5 immune response was detected in sera of mice immunized parenterally although no IgA were detected in BAL of those mice (FIG. 10B, left). Western analysis of protein extracts from plant- and bacterially expressed B5 (FIG. 10B, right) confirmed the B5 specificity of the mouse serum antibodies. FIG. 10C shows the B5-specific IgA type response in bronchoalveolar lavage (BAL) from mice when parenteral immunization was followed (busted) by the third mucosal immunization with pB5 protein. FIG. 10D shows the antigen-specific antibody response after three rounds (1$^{st}$, 2$^{nd}$, 3$^{rd}$) of intramuscular (i.m.) immunization with recombinant pL1 applied with together with alum/CpG adjuvant.

In addition to IgG in sera induction, B5-specific IgA was detected in BAL of intranasally immunized mice (FIG. 10C). Strong L1-specific immune response was detected in sera of mice immunized parenterally with pL1 protein (FIG. 10D).

In addition to the experiments with mice, immunogenicity of B5 protein was confirmed in the mini-pig by similar routes of immunization. Analysis of the immune response in the mini-pig revealed a pattern similar to that observed in mice. After feeding, no anti-B5-specific antibodies were detected in the serum, saliva, or vaginal secretions. However, after intranasal immunization with B5 together with CT, the serum showed an increase in B5-specific IgG. Sustained increase in B5-specific serum IgG was detected after i.m. immunization with purified pB5 in combination with CpG-ODN and alum (CpG/alum).

Example 6

Lethal Challenge with Vaccinia Virus (VV)

The level of protection in pB5-immunized mice was analyzed for the presence of B5-specific antibodies in sera by measuring the in vitro functional anti-VV activity and challenging the mice with a lethal dose of VV. Groups of mice were either vaccinated with VV once by tail scarification or immunized three times with plant-derived pB5 (in CpG/alum) i.m. Control mice were injected with extracts of plant total soluble protein (TSP) in CpG/alum or left unvaccinated. Three weeks after the third vaccination, sera were tested by ELISA (FIG. 11A) and in the comet inhibition assay (FIG. 11B) as a qualitative measure of anti-VV antibody activity. FIG. 11A (top) shows IgG titers detected in sera from mice immunized either with live Vaccinia virus vaccine (VV-Vac) or only with plant B5, both treatments included Cpg/alum adjuvant (Immunizations). FIG. 11A (bottom) shows the results for control groups injected with an adjuvant alone (CpG/alum) or wild type plant TSP, or left unvaccinated (Controls).

FIG. 11B shows characteristic visual results of "comet inhibition" assay formed by the VV, a standard in the area of research. The top panels show comet formation alterations caused by the B5 antibodies present in sera from mice immunized with pB5 protein together with the CpG/alum adjuvant (top left panel). Comet formation was completely inhibited by sera vaccinated with VV vaccine (top right panel). The control lower panels show that comet formation was not altered in negative control groups: (1) treated with TSP from a wild type plant and adjuvant (plant/CpG/alum, right panel), (2) treated with an adjuvant alone (CpG/alum, middle panel), and (3) unvaccinated (left panel).

Referring to FIGS. 11A and 11B, it was observed that the serum immune response in mice was equally pronounced when using either CpG/alum or Freund's as an adjuvant (compare FIG. 11A and FIG. 10C). As shown in FIG. 11B, sera from pB5-vaccinated mice altered comet formation (upper panel, left), and sera from VV-vaccinated mice inhibited comet formation completely (upper panel, right); control mouse sera did not alter comet formation (lower panel).

Vaccinated mice were then challenged intranasally with a lethal dose of VV and monitored daily for weight loss and morbidity (FIGS. 11C and 11D). These figures shows 100% positive survival results in live lethal challenge experiment with pB5 injections compared to the live vaccine application, placed in parallel for better visual comprehension. FIG. 11D shows the survival rate for the same groups of mice as shown in FIG. 11A. These mice subjected to the lethal intranasal challenge with VV conducted three weeks after the vaccination with plant B5; or, 7 weeks after a single time the vaccinia vaccine application by tail scarification. Once below the 30% initial weight loss (or morbid) mice were sacrificed.

Only the mice vaccinated with either VV or pB5 survived the challenge (FIG. 11D). Control naïve-, CpG/alum-, and non-transgenic plant material-vaccinated mice all died, indicating that survival is B5-dependent. Although 100% of the B5-vaccinated mice survived, they did experience a greater weight loss than the VV-vaccinated mice (FIG. 11C). Maximal weight loss (5%) was observed on day-3 post-challenge, whereas B5-vaccinated mice underwent a loss close to 30% on day-8 post-challenge.

Figure 12A:
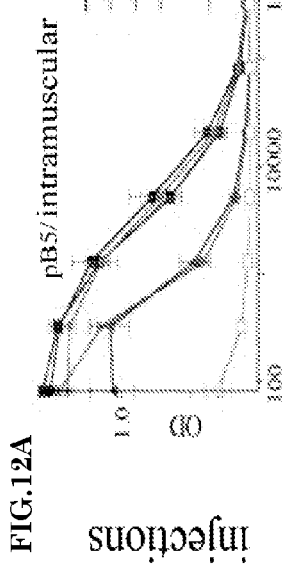
FIG. 12A illustrates data obtained for mice immunized i.m. with 1 µg of pB5 supplemented with increasing amounts of plant TSP.
Figure 12B:
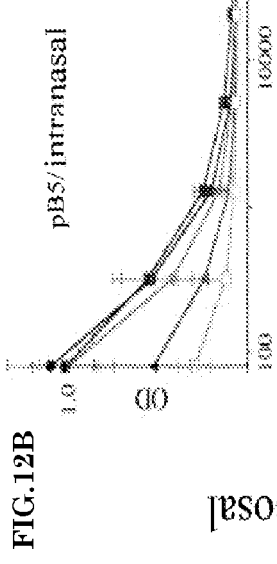
FIG. 12B illustrates data obtained for mice immunized i.n. with 1 µg of pB5 supplemented with increasing amounts of plant TSP.
Figure 12C:
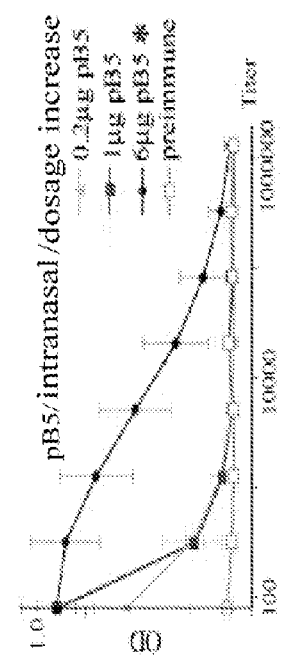
FIG. 12C illustrates data obtained for mice immunized i.n. with increasing amounts of pB5 (0.2-6 µg).
Figure 13A:
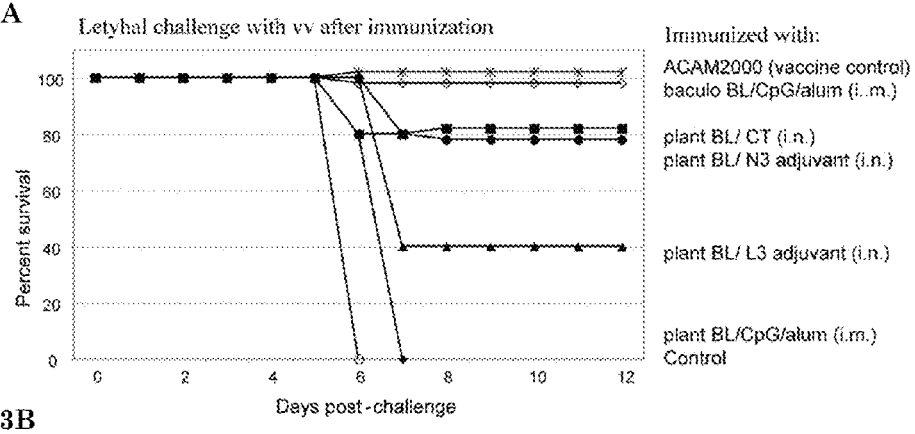
FIGS. 13A-13B illustrate that intranasal administration of a combination of B5- and L1-proteins protects mice from lethal challenge (i.n. with live vaccinia virus (VV)) based on survival rate (FIG. 13A) and weight loss (FIG. 13B) of the challenged mice.
Figure 13B:
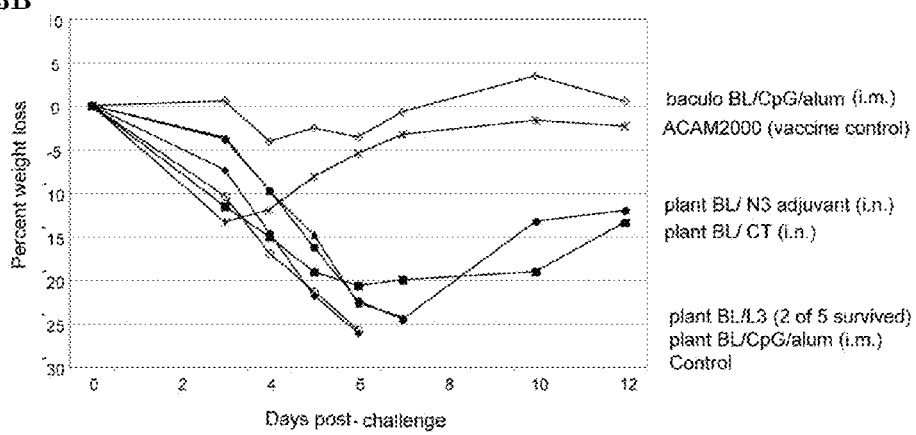
Figure 14:
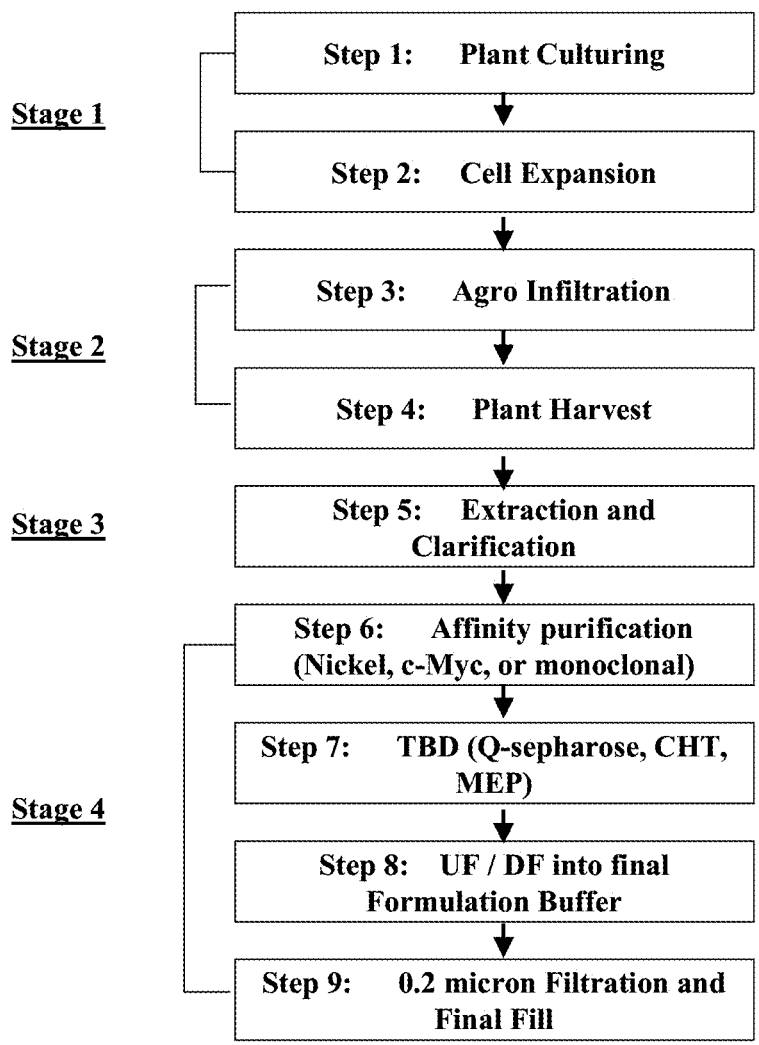
FIG. 14 illustrates steps of large scale production and purification of antigens. CHT means ceramic hydroxyapatite; MEP means MEP Hypercell resin.

The impact of the purity (with respect to contamination with plant total soluble protein—TSP) of plant-based pB5 vaccine preparations was analyzed when administered by different routes on antigen-specific antibody responses in mice and (FIG. 12). This figure shows the B5-specific serum IgG response measured as a function of TSP/B5 protein dose and systemic (parenteral) or local (mucosal) routes of administration. Detection results are shown as ELISA graphs (mean±S.D., left panel) and Western blots (right panel). Mice were immunized either intramuscular (i.m.) or intranasally (i.n.). The corresponding Western blot analyses were done using the resulted mice sera at 1:1000 dilutions. Protein samples were loaded at increasing concentrations: 0.25; 1.25 and 2.5 μg per lane for plant-derived B5, and 2.5; 5 and 10 μg per lane for wild type plant TSP. Arrows point from each figure toward the corresponding Western blot panel.

FIG. 12A shows the effect of plant TSP contaminants on i.m. immunization (injections) when administering standardized 1 μg of pB5. The threshold concentration of plant contamination versus the antigen that significantly affected the immune response was approximately 10×. FIG. 12B shows the affect of TSP contamination on i.n. immunization (mucosal) when administering standardized 1 μg of pB5 supplemented with increasing amounts of plant TSP. FIG. 12C shows that mice immunized i.n. with the increased amounts of pB5 (6 μg) demonstrated almost the same immune response as with 1 μg by injection Referring to these figures, it was observed that purified pB5 elicited a specific and strong serum IgG response, especially when administered i.m. (FIG. 12A, left), consistent with previous observations. The response after i.n. immunization at the same dose of pB5 (1 μg) was lower (FIG. 12B, left). When administered at 6 μg, pB5 induced IgG titers comparable to those obtained by i.m. immunization with 1 μg of pB5 (FIG. 12 C, left).

Western analysis of mouse sera with the highest IgG titers (FIG. 12C, right) revealed no plant-specific IgG accompanying the pB5-specific response after i.n. immunization. Addition of plant TSP at increasing concentrations to the i.m. immunizations with pB5 at 1 μg had no effect on pB5-specific IgG titers at TSP doses of 2 and 10 μg, whereas addition of 30 and 50 μg TSP led to a 25% decline in titers (FIG. 12A, left). The titers of pB5-specific IgG after i.n. immunization were negatively affected by TSP at 20 μg (FIG. 12B, left). Western analysis (FIGS. 12A and 12B, right) of representative serum samples obtained after i.m. immunization confirmed the presence of antigen-specific antibodies as well as antibodies against some plant proteins.

Overall data indicate a high sensitivity of an immune response to antigen purity (TSP contamination) especially when the antigen is applied mucosally.

Based on these data from mucosally immunized mice a pilot challenge experiment in mice immunized intranasally has been conducted, using preparations of both pB5 and pL1 proteins. Additionally, cholera toxin (CT) and two potent mucosal adjuvants were used in administered composition. These adjuvants represent efficient lipid-based mucosal adjuvants that were successfully tested in animal models and human clinical trials. The protection from virus lethal challenge was observed after the needle-free intranasal (mucosal) administration when using a combination of pB5- and pL1 proteins (FIGS. 13A-13B). Mice were immunized i.n. with 3 times/2 weeks intervals with a combination of B5 and L1 proteins (3 μg each) supplemented with oil-based adjuvants (Eurocine, Sweden), 5 μl each or 1 μg of CT. Control groups received either live vaccinia virus vaccine or left unvaccinated. Mice were challenged i.n. with live VV and monitored for survival rate (FIG. 13A) and weight loss (FIG. 13B).

Data herein indicate that intranasal immunization with the two (pB5 and pL1) plant-derived antigens can protect mice against the lethal challenge. Furthermore, the levels of protection achieved using novel oil-based adjuvants are comparable to those obtained with CT. This finding is in agreement with a study that showed that mice can be protected against lethal challenge by intranasal immunization with killed vaccinia virus vaccine.

Example 5

Large Scale Production and Purification of Antigens

Plant-based compositions of the present invention are useful for preindustrial and industrial scale production of drug products.

Pilot extraction experiments using a two-step affinity purification process resulted in average yields of 100 μg pB5 and 300 μg pL1 from grams of lyophilized plant tissue. The small-scale optimization experiments results in 10-100 grams of plant material and directly corresponds to parameters will be tested with large scale experiments (>10-50 kg of plant fresh tissue material for each antigen). As a result of large scale production at least 100 mg of each antigen (purity>99%) may be obtained.

The production, processing, and purification of the pA33, pB5, and pL1 antigens are depicted in FIG. 14, the schematic flow diagram of the manufacturing process. Referring to this figure, Stage 1 includes the growth of wild-type *N. benthamiana* plants and *Agrobacterium* (Agro) inoculums amplification that contains plant transformation Magnifection plasmids. Freshly grown *Agrobacterium* cell cultures are diluted to be utilized at the next stage. Stage 2 includes vacuum infiltration of *N. benthamiana* with *Agrobacterium* suspension, plant growth until harvest, usually for a week or two, to reach optimum expression and accumulation of immunogenic proteins in plants. Stage 3 includes extraction and clarification of the plant extracts. Stage 4 includes downstream steps up to step 9; with affinity purification, step 6, determined upon the prior optimization results; polishing, step 7, determined upon the efficiency of removal of the host cell proteins and endotoxins, step 8, ultrafiltration and diafiltration (UF/DF) into the final formulation buffer prior to vialing. Processing and operations for Stage 4 are to be conducted in Class 10,000 manufacturing suites.

Purified antigen is characterized by release assays, for example, concentration by UV absorption; identity by isoelectric focusing; purity by SDS-PAGE; aggregation/degradation by SEC-HPLC; endotoxin levels and bioburden, all of which are known for the skilled artisan.

Concurrently, real time and accelerated stability studies are performed to assess product stability and to select an initial formulation for storage at −80° C. A matrix study may be performed in which antigens are tested weekly at 3 concentrations at four temperatures (−20, 4, 25, and 400° C.), at pH ranges (pH 5-8) with varying concentrations of methionine (to prevent oxidation) and Tween (to reduce aggregation) over eight weeks. From these four stages of production, a single bulk lot of each antigen is obtained.

Stability is assessed by ELISA and SDS-PAGE electrophoresis, and aggregation is monitored by size exclusion chromatography. Peptide mapping may be performed and peptides may be evaluated by liquid chromatography mass spectrometry (LC/MS/MS) to assess potential post-translational modifications such as oxidation and deamidation. The conditions with the most favorable stability profile may be used then for cGMP manufacturing.

Example 6

Immunological Assessment of Plant-Derived Immunogenic Composition in Mice

Once the industrial production of highly purified plant-derived antigenic material is established experimentally determination is made: i) on optimal dosing of antigens; ii) whether mucosal (needle-free) immunization together with new and highly potent mucosal adjuvants can provide 100% protection to mice against vaccinia challenge.

The intranasal route, in addition to being needle-free, is appealing because of the possibility to induce mucosal IgA, which may provide a mucosal barrier, in contrast to a systemic response that protects mice after virus has breached mucosal surfaces. Such a route of vaccination may result in better protection than parental vaccination. However, there are several possible complications associated with this approach that needs to be overcome: the intranasal route may produce a weaker immune response or require a prohibitively high dose of antigen to produce sufficient levels of IgG/IgA. It also requires specific adjuvants (such as CT used in preliminary experiments) suitable for human use.

Adjuvants are used as a component for subunit/recombinant vaccines, added to improve immune response, increase antibody titers; reduce the antigen dose and number of doses needed; enable immunization in patients with weakened immune systems; provide appropriate bias and induce cell-mediated immunity. Adjuvants currently approved for global use include aluminum (alum); MF59 (squalene emulsion); AS03 (squalene/tocopherol emulsion); AF3 (squalene emulsion; Virosomes (liposomes)); and polyoxidonium (polyelectrolyte). Alum adjuvants are widely used in pediatric vaccines including DTP, Hepatitis B virus and pneumococcal vaccines because they enhance titers and they have a long record of safety. The drawback with alum adjuvants is that they are not really suitable for yearly administration because the adjuvant effect is dependent on many factors. Oil-in-water emulsions are simply droplets of oil in water (~100 nm), the most common of which are squalene & tocopherol and Tween/lecithin. The MF59 adjuvant (Novartis) is made from squalene in water with Tween/Span and has been used in influenza vaccines in European countries since 1996. The push toward development of the MF59 adjuvant began with the last emergence of H5N1 because it required an enormously large dose of antigens needed to get an immune response. In 2009, when MF59 was incorporated into the 2009 H1N1 pandemic vaccine, it increased global vaccine production capacity to more than 200 million doses distributed for all ages. The caveat is that there is an increase in local reactogenicity, some local site reactions and some redness.

Test experiments should reveal the suitability of novel mucosal adjuvants. One example being recently developed for a new generation of nasal vaccines has been already tested in human clinical trials.

Example 7

General Protocols Used for Production, Testing Immunization Routes and Dosages

The Magnifection transient expression system was established and confirmed relatively high yields of production of recombinant material. The empirical evaluation of genetically engineered expression cassettes for pAL1, pB5, pA33 confirmed production of recombinant antigenic proteins. These proteins may be optimized and used for preparative and large scale production. The proteins preparations may also be used to evaluate stability of recombinant protein(s) in the purification process and/or storage.

The genetic engineering arrangements and gene codon optimization are meant to achieve higher yields and help to retain proper glycosylation/folding of viral glycoprotein important in getting specific and pronounced immune response. Sufficient amounts of antigens may be available for animal experiments. The affinity chromatography option may be considered, to use *N. benthamiana*-produced mAb's against the pA33, pB5, and pL1. At this stage additional steps may be conducted with lower grade antigens (e.g. 90-95% pure) while working to improve the purity of the product to 99%.

A reliable immunization protocol that provides 100% protection in mice (w/o any transient weight loss) against a lethal challenge with VV was established, using plant derived antigens. The disproportional immune responses against the antigens when used in a mixture require optimizing the proportion of individual components empirically (formulation studies) and necessitate repeating some immunization experiments in mice. Six- to eight-week-old female BALB/c mice (5 or 10 mice per group) are used in all experiments as follows:

Intranasal immunization: the efficiency of intranasal delivery will be tested with the material comprising all three antigens at optimal doses and adjuvant. 5 μl of antigen(s) in saline is mixed with several potential candidate adjuvants and administered into both nostrils. Blood and fecal matter is collected 10 days after each immunization (or as indicated). These experiments require 40 Balb/c mice. Proteins from fecal pellets is extracted in PBS (10 vol/wt) supplemented with 1% BSA and protease inhibitors. Mice is killed 10 days after the last immunization (or as indicated) and bled by cardiac puncture, and sera is analyzed as indicated. The immune response against each protein is checked in sera by ELISA and in vitro virus neutralization tests as described below. The IgA response in BAL and fecal pellets is checked as well. The appearance of IgA in the lungs was previously confirmed and is thought to add to the overall level of protection.

Parenteral immunization: antigen(s) are administered intramuscularly with either aluminum hydroxide (alum) along or with CpG oligodeoxynucleotides (ODN) (SEQ ID NO: 22: TCCATGACGTTCCTGACGTT) and alum combination as an adjuvant (CpG/alum) at 50 μg per mouse. Immunization is performed 3 times at 2 week intervals. Four different doses of each antigen per mouse/per immunization (5, 10, 20, and 30 μg) were evaluated for the optimal amount with a total of 50 mice including all appropriate controls.

Parenteral Plus Mucosal Vaccination:

mice received an optimal priming dose of antigen by intramuscular injection in combination and then, at different time points (1, 2 and 3 months), boosted with the same antigen mixture (at higher doses: 5, 10, 50 and 100 μg per mouse) by the intranasal route using mucosal adjuvants.

Around 40-60 animals are required to do the optimization of the priming-boost doses in regards to the strength (and, if possible, duration) of the obtained response. Animals are sacrificed ten days after the last boosting dose and the immune response against each protein will be checked in sera (IgG), BAL and fecal pellets (IgA) by ELISA, as described [8]. The optimized protocol is used to carry out challenge and virus neutralization experiments. Groups of mice immunized with suboptimal protocols (parenteral and mucosal) are included for comparison and symptom analysis (IgG/IgA versus IgG alone).

Optimization of Vaccine Formulation for Mucosal Delivery:

this experiment tests the longevity of systemic IgG and mucosal IgA response. The immunization protocol (e.g. parenteral, parenteral/mucosal, or mucosal only) for this experiment will be established based on the data from previous experiments. Groups of 5 mice are sacrificed monthly during a 6 month period and serum IgG and BAL/fecal pellets IgA monitored by ELISA. If titers drop by 80%, another mucosal boost may be given and monitoring continues for the remaining animals. As a result, the duration of the immune response induced by this protocol with plant-produced antigens is established. 30 mice are required to reach this goal. The best vaccination protocols are evaluated in vitro and in vivo and concluded by the challenge experiment with live virus. The level of protection is compared, as previously, with the one obtained by immunization with a live, non-virulent strain of vaccinia virus done by standard parenteral route protocol. 40 mice will be used in this experiment.

Bronchoalveolar Lavage (BAL):

After exsanguinations, mice are incised ventrally along the midline and the trachea exposed. A 21 g blunt needle hub is introduced into the trachea and 0.6 ml of normal NaCl injected into the lungs. After 1 minute, the fluid is aspirated and frozen at −20° C. Prior to analysis, samples are centrifuged and cleared of cells debris. Total protein content is quantified using Nanodrop measurements at 280. Protein content in samples usually averages around 0.4 mg/ml.

VV Lethal Challenge:

Three weeks after the last protein vaccination, mice are challenged intranasally with $1.2\times10^6$ pfu of VV (strain WR) in 20 μl of sterile PBS. Mice are weighed and monitored each day. Animals that appear morbid or have lost >30% of their initial body weight are sacrificed in accordance with the institutional guidelines for animal welfare [18].

Comet Inhibition Assay:

The in vitro assay is performed as described in [18]. A confluent monolayer of BSC-1 cells grown in 12-well plates is infected with VV strain IHDJ at 5 pfu per well for 2 h at 37° C. The inoculums' is removed and 1 ml of fresh MEM medium containing 2.5% FCS and 25 μl (1:40 dilution) of pooled sera obtained from mice 3 weeks after the last boost vaccination (just before challenge) is added. Plates will be incubated for 36 h at 37° C. and stained with 0.2% crystal violet in 4% ethanol, and photographed.

It is understood, therefore, that this invention is not limited to the particular embodiments disclosed, but is intended to cover all modifications which are within the spirit and scope of the invention as defined by the appended claims; the above description; and/or shown in the attached drawings.

The references cited throughout this application, are incorporated by reference for all purposes stated or apparent herein as if each reference was fully set forth. A citation of a reference at a particular location indicates an exemplary manner in which the teachings of the reference are incorporated, without limitation on the incorporation of the full teachings of the reference.

What is claimed is:

1. A method for producing a plant-derived immunogenic composition comprising:
   contacting a plant with a first polynucleotide encoding a first immunogenic protein and a second polynucleotide encoding a second immunogenic protein, wherein each of the first immunogenic protein and the second immunogenic protein elicits an immune response in a subject against poxvirus, wherein the first polynucleotide includes a sequence with at least 98% identity to a sequence of SEQ ID NO: 6, and the second polynucleotide includes a sequence with at least 98% identity to a sequence of SEQ ID NO: 8; and
   culturing the plant under conditions effective for expressing the first immunogenic protein and the second immunogenic protein.

2. The method of claim 1 further comprising contacting the plant with a third polynucleotide encoding a third immunogenic protein capable of eliciting an immune response in a subject against poxvirus, and culturing under conditions effective for expressing the third immunogenic protein.

3. The method of claim 2 further comprising isolating and purifying the first immunogenic protein, and at least one of the second immunogenic protein and the third immunogenic protein from the plant.

4. The method of claim 2, wherein the third immunogenic protein is an A33 protein.

5. The method of claim 2, wherein the third polynucleotide includes a sequence with at least 90% identity to a reference sequence of SEQ ID NO: 10.

6. The method of claim 2, wherein the first polynucleotide and at least one of the second polynucleotide or the third polynucleotide are included in a vector providing for stable transformation of a plant or transient expression in a plant.

7. The method of claim 6, wherein the vector is at least one of a tobacco mosaic virus-based vector and a potato virus X-based vector.

8. The method of claim 1 further comprising providing an adjuvant.

9. The method of claim 1 further comprising providing a pharmaceutically acceptable carrier.

* * * * *

SEQUENCE LISTING

```
<160> NUMBER OF SEQ ID NOS: 23

<210> SEQ ID NO 1
<211> LENGTH: 16
<212> TYPE: DNA
<213> ORGANISM: Artificial Sequence
<220> FEATURE:
<223> OTHER INFORMATION: Synthetic construct, Kawazaki sequence

<400> SEQUENCE: 1
ccatggaaca aaaatg                                                   16

<210> SEQ ID NO 2
<211> LENGTH: 18
<212> TYPE: DNA
<213> ORGANISM: Artificial Sequence
<220> FEATURE:
<223> OTHER INFORMATION: Synthetic construct, Hind III Restriction site

<400> SEQUENCE: 2
aagcttaatt aagaattc                                                 18

<210> SEQ ID NO 3
<211> LENGTH: 33
<212> TYPE: PRT
<213> ORGANISM: Artificial Sequence
<220> FEATURE:
<223> OTHER INFORMATION: Synthetic construct, APBP1 peptide
```

-continued

```
<400> SEQUENCE: 3

Met Ile Val Leu Ser Val Gly Ser Ala Ser Ser Pro Ile Val Val
1               5                   10                  15

Val Phe Ser Val Ala Leu Leu Leu Phe Tyr Phe Ser Glu Thr Ser Leu
                20                  25                  30

Gly

<210> SEQ ID NO 4
<211> LENGTH: 24
<212> TYPE: PRT
<213> ORGANISM: Artificial Sequence
<220> FEATURE:
<223> OTHER INFORMATION: Synthetic construct, BAA peptide

<400> SEQUENCE: 4

Met Ala Asn Lys His Leu Ser Leu Ser Leu Phe Leu Val Leu Leu Gly
1               5                   10                  15

Leu Ser Ala Ser Leu Ala Ser Gly
                20

<210> SEQ ID NO 5
<211> LENGTH: 11
<212> TYPE: PRT
<213> ORGANISM: Artificial Sequence
<220> FEATURE:
<223> OTHER INFORMATION: Synthetic construct, flexible linker

<400> SEQUENCE: 5

Ser Lys Ser Trp Asn Arg Ala Gln Phe Gly Ser
1               5                   10

<210> SEQ ID NO 6
<211> LENGTH: 981
<212> TYPE: DNA
<213> ORGANISM: Artificial Sequence
<220> FEATURE:
<223> OTHER INFORMATION: Synthetic construct, Pg1

<400> SEQUENCE: 6
ccatggcttg aaacaaaaat gattgtgctt tctgtgggat ctgcttcttc tagtcctatc      60
gtggtggttt tctctgtggc attactcctc ttctatttct ctgaaacatc tttaggttgt     120
accgttccta ctatgaataa cgctaagttg actagtacag agacctcttt taatgataag     180
caaaaggtta ctttcacatg tgatcaggga taccattctt cagatcctaa tgcagtgtgc     240
gagactgata agtggaaata tgaaaaccct tgtaagaaaa tgtgcacagt tcagattac      300 atcagtgagc tctacaataa gcctctctat gaagtgaact ctaccatgac tctttcatgt     360
aatggtgaaa caaagtactt tagatgcgaa gaaaagaatg gtaacacctc atggaatgat     420
acagttacct gtcctaacgc tgagtgccaa ccacttcagt tggaacatgg ttcatgtcaa     480
ccagtgaagg agaagtacag tttcggagaa tacatgacaa ttaattgtga tgttggttac     540
gaagtgattg gagctagtta tatctcttgc actgcaaata gttggaacgt tattccttct     600
tgtcaacaga gtgcgatat gccatcactt agtaatggtt tgatctctgg atcaacattt     660
tctattggtg gagttatcca ccctttcatg caagagtggt tcacttttgac aggatcacca     720 agttctactt gtattgatgg aaagtggaat cctgttcttc caatctgcgt gaggaccaac     780
gaagagtttg atcctgttga tgatggacca gatgatgaga ctgatctttc taagctctca     840
aaagatgttg tgcaatacga acaggagatt gaatctttgg aagcaactta tcatcaccat     900
```

| caccaccact caaaaagttg aatagagca cagttcggtt cacatcatca tcatcatcac | 960 |
| taaaagctta attaagaatt c | 981 |

<210> SEQ ID NO 7
<211> LENGTH: 949
<212> TYPE: DNA
<213> ORGANISM: Artificial Sequence
<220> FEATURE:
<223> OTHER INFORMATION: Synthetic construct, Pg1.1

<400> SEQUENCE: 7

| ccatggaaca aaaatggcta acaaacactt atcactctca ctctttctcg tgctccttgg | 60 |
| actctccgct tcacttgctt ctggatgtac tgtgcctact atgaataacg ctaaacttac | 120 |
| tagtacagag acttccttta acgataagca aaaggttaca ttcacttgtg atcagggata | 180 |
| ccattcttca gatccaaatg cagtgtgcga gactgataag tggaaatatg aaaaccttg | 240 |
| taagaaaatg tgcactgttt ctgattacat ctcagagctc tacaacaaac cactctatga | 300 |
| agtgaacagt acaatgactt tgtcctgtaa tggagagaca aagtacttta gatgcgaaga | 360 |
| gaaaaatggt aacacttctt ggaatgatac agttacttgt ccaaacgctg agtgccaacc | 420 |
| tcttcagttg gaacatggat catgtcaacc tgtgaaggag aagtacagtt cggtgaata | 480 |
| catgacaatc aactgtgatg ttggatacga agtgatcggt gcttcttata tttcatgcac | 540 |
| tgcaaatagt tggaacgtta ttccatcttg tcaacagaag tgcgatatgc cttctctttc | 600 |
| aaacggattg ataagtggtt ccacattttc tattggaggt gttatacacc ttagttgtaa | 660 |
| gtccggattc acattgactg gttcaccaag ttccacttgt atagatggaa aatggaatcc | 720 |
| agttttacct atctgcgtga ggacaaacga agagtttgat ccagttgatg atggtcctga | 780 |
| tgatgagact gatttatcta agctctcaaa agatgttgtg caatacgaac aggagattga | 840 |
| atcacttgaa gcaacatatc atcaccatca ccaccactca aaatcctgga atagggctca | 900 |
| gttcggaagt caccatcatc atcaccacta aaagcttaat taagaattc | 949 |

<210> SEQ ID NO 8
<211> LENGTH: 762
<212> TYPE: DNA
<213> ORGANISM: Artificial Sequence
<220> FEATURE:
<223> OTHER INFORMATION: Pg 2

<400> SEQUENCE: 8

| ccatggcttg aaacaaaaat gattgtgctt tctgtgggat ctgcttcttc tagtcctatc | 60 |
| gtggtggttt tctctgtggc attactcctc ttctatttct ctgaaacatc tttaggtgga | 120 |
| gcagcagcat caatccagac taccgtgaac accttatcag aaagaatctc atcaaaactc | 180 |
| gaacaggagg caaacgcatc agcacaaacc aagtgtgata tcgaaatcgg taacttctac | 240 |
| atcagacaga atcatggatg taacttaaca gttaaaaaca tgtgctctgc tgatgcagat | 300 |
| gctcaacttg atgctgtgtt gtcagctgca actgaaacat atagtggttt aactcctgag | 360 |
| caaaaggcat acgttccagc tatgtttaca gctgcactca atattcagac ctcagttaac | 420 |
| actgttgtga gggatttcga gaactacgtg aaacaaactt gtaactcttc agcagttgtg | 480 |
| gataataagt tgaagatcca aacgttatt atcgatgaat gctacggtgc tcctggatct | 540 |
| ccaacaaatc ttgagttcat taacaccggt agttctaagg gaaattgcgc tattaaggct | 600 |
| cttatgcagc tcacaaccaa ggcaacaacc caatcgcac caaacaagt ggcaggtaca | 660 |
| ggagttcagc atcatcacca tcaccaccac tcaaaaagtt ggaatagagc acagttcggt | 720 | tcacatcatc atcatcatca ctaaaagctt aattaagaat tc          762

<210> SEQ ID NO 9
<211> LENGTH: 727
<212> TYPE: DNA
<213> ORGANISM: Artificial Sequence
<220> FEATURE:
<223> OTHER INFORMATION: Synthetic construct, Pg2.2

<400> SEQUENCE: 9
ccatggaaca aaaatggcaa acaaacatct ctccttatct cttttcttag tgctcttggg     60
tctttctgca tccctcgctt caggtggtgc tgctgcttct atccaaacta cagttaacac    120
tctttctgaa agaatctctt caaagttgga acaagaggct aatgcatcag ctcagacaaa    180
gtgtgatatc gagatcggaa acttctacat caggcaaaat catggttgta acttgactgt    240
taagaacatg tgcagtgcag atgctgatgc acagttagat gctgtgctca gtgctgcaac    300
tgaaacatat tccggattaa ctccagagca aaaggcttac gttcctgcaa tgtttacagc    360
tgcattgaat atccagactt ctgttaacac agttgtgaga gatttcgaaa actacgtgaa    420
gcaaacatgt aacagttccg cagttgtgga taacaaactt aagatccaga acgttataat    480
agatgaatgc tacggagctc aggttctcc tactaatctt gagttcatta acacaggatc    540
ttcaaagggt aattgcgcta tcaaagcact tatgcaattg actacaaagg ctactacaca    600
aattgcacca aaacaggttg ctggaactgg tgtgcagcat caccatcacc atcacagtaa    660
atcctggaat agagcacagt tcggttcaca ccatcatcat caccactaaa agcttaatta    720
agaattc                                                              727

<210> SEQ ID NO 10
<211> LENGTH: 591
<212> TYPE: DNA
<213> ORGANISM: Artificial Sequence
<220> FEATURE:
<223> OTHER INFORMATION: Synthetic construct, Pg3

<400> SEQUENCE: 10
ccatggcttg aaacaaaaat gattgtgctt tctgtgggat ctgcttcttc tagtcctatc     60
gtggtggttt tctctgtggc attactcctc ttctatttct ctgaaacatc tttaggtagg    120
ctcaatcagt gtatgtctgc taacgaggct gcaatcaccg atgctgctgt ggctgtggct    180
gctgcttctt caacccatag gaaagttgct tcttcaacta cacaatacga tcataaggaa    240
tcatgtaatg gtctttacta ccaaggatca tgctacatct tacacagtga ttaccagctc    300
ttttctgatg ctaaggcaaa ttgtacagca gaaagttcta ccttgcctaa caaatctgat    360
gttcttatca cttggttgat cgattacgtg gaggatacat ggggttcaga tggaaaccca    420
atcaccaaaa ccactagtga ttaccaagat agtgatgtta gtcaagaagt gaggaagtat    480
ttttgcgtga agaccatgaa ccatcaccat caccaccact caaaaagttg gaatagagca    540
cagttcggtt cacatcatca tcatcatcac taaaagctta attaagaatt c             591

<210> SEQ ID NO 11
<211> LENGTH: 559
<212> TYPE: DNA
<213> ORGANISM: Artificial Sequence
<220> FEATURE:
<223> OTHER INFORMATION: Synthetic construct, Pg3.3

<400> SEQUENCE: 11

```
ccatggaaca aaaatggcta acaaacatct ctccctctcc ctcttcttgg tgctcctcgg    60
actcagtgca tccttggcat caggtagact caatcagtgc atgtcagcaa atgaagctgc   120
aatcacagat gctgcagttg ctgtggctgc agcttcttca actcatagaa aggttgcaag   180
ttccactaca caatatgatc acaaagagag ttgtaacgga ctttactacc aaggttcttg   240
ctacatcctc cattcagatt accagctctt tagtgatgca aaggctaatt gtactgctga   300
atcttcaaca ttgccaaaca agtcagatgt tcttatcact tggttgatcg attacgtgga   360
ggatacatgg ggatctgatg gtaaccctat cactaagact acatctgatt accaagatag   420
tgatgtttcc caggaagtga ggaagtactt ctgcgtgaaa acaatgaacc atcaccatca   480
ccaccactct aaatcctgga atagggcaca gttcggtagt caccatcacc accaccattg   540
aaagcttaat taagaattc                                                559
```

```
<210> SEQ ID NO 12
<211> LENGTH: 19
<212> TYPE: PRT
<213> ORGANISM: Artificial Sequence
<220> FEATURE:
<223> OTHER INFORMATION: Synthetic construct, Tobacco optimized peptide

<400> SEQUENCE: 12

Glu Gln Lys Leu Ile Ser Glu Glu Asp Leu His His His His His His
1               5                   10                  15

Asp Glu Leu
```

```
<210> SEQ ID NO 13
<211> LENGTH: 25
<212> TYPE: PRT
<213> ORGANISM: Artificial Sequence
<220> FEATURE:
<223> OTHER INFORMATION: Synthetic construct, Homo sapiens optimized
      peptide

<400> SEQUENCE: 13

His His His His His His Glu Gln Lys Leu Ile Ser Glu Glu Asp Leu
1               5                   10                  15

His His His His His His Asp Glu Leu
            20                  25
```

```
<210> SEQ ID NO 14
<211> LENGTH: 867
<212> TYPE: DNA
<213> ORGANISM: Artificial Sequence
<220> FEATURE:
<223> OTHER INFORMATION: Synthetic construct, Pg1.2

<400> SEQUENCE: 14
catgggttgc actgtgccta ccatgaacaa cgctaagttg accagcaccg agacatcctt    60
caacgataag caaaaggtga ccttcacttg cgatcagggt taccacagct ctgatcctaa   120
tgctgtgtgc gagactgata gtggaagta cgagaaccct tgcaagaaga gtgtgcaccgt   180
tagcgattac atcagcgagc tgtacaacaa gcctctgtac gaggtgaact ctaccatgac   240
cctttcatgc aacggtgaga ctaagtactt caggtgcgaa gagaagaacg gtaacaccag   300
ctggaatgat actgtgacct gccctaatgc tgagtgccaa cctcttcagc ttgagcatgg   360
ttccttgcca gcctgtgaaag aaagtacag cttcggtgag tacatgacca tcaactgtga   420
tgtgggttac gaggtgatcg gtgctagcta catttcttgc accgctaaca gctggaacgt   480
gatcccatct tgtcagcaaa agtgcgatat gcctagcctg agcaacggtc tgattagcgg   540
```

```
ttctaccttc tctatcggtg gtgtgattca cctgagctgc aagtctggtt ttaccctgac    600
tggtagccct agctctacct gcattgatgg taagtggaac cctgtgcttc ctatctgcgt    660
gaggactaac gaagagttcg atcctgtgga tgatggtcct gatgatgaga ctgatctgag    720
caagctgtcc aaggatgttg tgcagtacga gcaagagatc gagtctttgg aggctaccta    780
cgagcagaag ctgatctctg aagaggatct tcatcaccat caccaccacg atgagctgta    840
gaagctttta attaagaatt cgagctc                                       867

<210> SEQ ID NO 15
<211> LENGTH: 772
<212> TYPE: DNA
<213> ORGANISM: Artificial Sequence
<220> FEATURE:
<223> OTHER INFORMATION: Synthetic construct, Pg1.3

<400> SEQUENCE: 15
ccatgggctg caccgtgccc accatgaaca cgccaagct gaccagcacc gaaaccagct      60
tcaacgacaa gcagaaagtg accttcacct gtgaccaggg ctaccacagc agcgacccca   120
acgccgtgtg cgagacagac aagtggaagt acgagaaccc ctgcaagaaa atgtgcaccg   180
tgtccgacta catcagcgag ctgtacaaca gcccctgta cgaagtgaac agcaccatga   240
ccctgagctg caacggcgag acaaagtact tcagatgcga ggaaaagaac ggcaacacca   300
gctggaacga caccgtgacc tgccccaatg ccgagtgcca gcccctgcag ctggaacacg   360
gctcctgcca gcccgtgaaa gagaagtaca gcttcggcga gtacatgacc atcaactgcg   420
acgtgggcta cgaagtgatc ggcgccagct acatcagctg caccgccaac agctggaatg   480
tgatccctag ctgccagcag aaatgcgaca tgcccagcct gagcaacggc ctgatcagcg   540
gcagcacctt cagcatcggc ggcgtgatcc acctgtcctg caagagcggc ttcacactga   600
ccggcagccc cagcagcacc tgtatcgacg gcaagtggaa cccgtgctg cccatctgcg   660 tgcggaccca ccaccaccat caccacgagc agaagctgat cagcgaagag gacctgcacc   720
atcatcacca tcacgatgag ctgtgaaagc ttttaattaa gaattcgagc tc             772

<210> SEQ ID NO 16
<211> LENGTH: 643
<212> TYPE: DNA
<213> ORGANISM: Artificial Sequence
<220> FEATURE:
<223> OTHER INFORMATION: Synthetic construct, Pg2.1

<400> SEQUENCE: 16
ccatgggtgc tgctgcttct attcagacta ccgtgaacac cctgagcgag aggattagct     60
ctaagttgga gcaagaggct aacgcttctg ctcagaccaa gtgcgatatc gagatcggta   120
acttctacat caggcagaac cacggttgca acctgaccgt gaagaatatg tgcagcgctg   180
atgctgatgc tcagccttga tgctgttcttt ctgctgctac cgagcttac tctggtctta   240 ccctgagca aaaggcttac gtgccagcta tgttcaccgc tgctcttaac attcagacct   300
ctgtgaatac cgtggtgagg gatttcgaga actacgtgaa gcagacctgc aactcttctg   360
ctgtggtgga taacaagctg aagatccaga acgtgatcat cgatgagtgc tacggtgctc   420
ctggttctcc tactaacctt gagttcatca acaccggtag cagcaaggga aactgcgcta   480
ttaaggctct tatgcagctg accactaagg ctaccactca gatcgctcct aagcaggttg   540
caggtactgg tgtgcaagag cagaagctga tctctgaaga ggatcttcat caccatcacc   600
```

```
accacgatga gctgtagaag cttttaatta agaattcgag ctc              643
```

<210> SEQ ID NO 17
<211> LENGTH: 667
<212> TYPE: DNA
<213> ORGANISM: Artificial Sequence
<220> FEATURE:
<223> OTHER INFORMATION: Synthetic construct, Pg2.3

<400> SEQUENCE: 17

```
ccatgggcgc tgccgccagc atccagacca ccgtgaacac cctgagcgag cggatcagca    60
gcaagctgga acaggaagcc aacgccagcg cccagaccaa gtgcgacatc gagatcggca   120
acttctacat ccggcagaac cacggctgca acctgaccgt gaagaacatg tgcagcgccg   180
acgccgacgc ccagctggat gctgtgctga gcgccgccac cgagacatac agcggcctga   240
cccccgagca gaaagcctac gtgcccgcca tgttcacagc cgccctgaac atccagacat   300
ctgtgaatac cgtggtccgc gacttcgaga actacgtgaa gcagacctgc aacagcagcg   360
ccgtggtgga caacaagctg aagatccaga acgtgatcat cgacgagtgc tacggcgctc   420
ccggcagccc caccaacctg gagttcatca acaccggcag cagcaagggc aactgcgcca   480
tcaaggccct gatgcagctg accaccaagg ccaccaccca gatcgccccc aaacaggtgg   540
ccggcaccgg cgtgcagttc taccaccacc accatcacca cgagcagaag ctgatcagcg   600
aagaggacct gcaccatcat caccatcacg atgagctgtg aaagctttta attaagaatt   660
cgagctc                                                             667
```

<210> SEQ ID NO 18
<211> LENGTH: 478
<212> TYPE: DNA
<213> ORGANISM: Artificial Sequence
<220> FEATURE:
<223> OTHER INFORMATION: Synthetic construct, Pg3.2

<400> SEQUENCE: 18

```
ccatgggtag gcttaaccag tgcatgtctg ctaacgaggc tgctattact gatgctgctg    60
ttgctgttgc tgctgcatct agcactcata ggaaggtggc atcttctacc acccagtacg   120
atcacaaaga gagctgcaac ggtctgtact accagggatc ttgctacatc ctgcacagcg   180
attaccagct gttctccgat gctaaggcta actgcactgc tgagtcctct accctgccta   240
acaagtctga tgtgcttatc acctggctga tcgattacgt tgaggatacc tggggttccg   300
atggtaaccc tattaccaag accacctccg attaccagga ttccgatgtg tctcaagagg   360
tgaggaagta cttctgcgtt aagaccatga acgagcagaa gctgatcagc gaagaggatc   420
ttcatcacca tcaccaccac gatgagctgt agaagctttt aattaagaat tcgagctc     478
```

<210> SEQ ID NO 19
<211> LENGTH: 496
<212> TYPE: DNA
<213> ORGANISM: Artificial Sequence
<220> FEATURE:
<223> OTHER INFORMATION: Synthetic construct, Pg3.1

<400> SEQUENCE: 19

```
ccatgggccg gctgaaccag tgcatgagcg ccaacgaggc cgccatcaca gatgccgccg    60
tggccgtggc cgctgccagc agcacacaca gaaaggtggc cagctccacc acccagtacg   120
accacaaaga gagctgcaac ggcctgtact accagggcag ctgctacatc ctgcacagcg   180
actaccagct gttcagcgac gccaaggcca actgcaccgc cgagagcagc accctgccca   240
```

```
acaagagcga cgtgctgatc acctggctga tcgactacgt ggaagatacc tggggcagcg    300
acggcaaccc catcaccaag accaccagcg attaccagga cagcgacgtg tcccaggaag    360
tgcggaagta cttctgcgtg aaaaccatga accaccacca ccatcaccac gagcagaagc    420
tgatcagcga agaggacctg caccatcatc accatcacga tgagctgtga aagcttttaa    480
ttaagaattc gagctc                                                    496

<210> SEQ ID NO 20
<211> LENGTH: 19
<212> TYPE: DNA
<213> ORGANISM: Artificial Sequence
<220> FEATURE:
<223> OTHER INFORMATION: Synthetic construct, NPTII forward primer

<400> SEQUENCE: 20
tgaatgaact gcaggacga                                                 19

<210> SEQ ID NO 21
<211> LENGTH: 19
<212> TYPE: DNA
<213> ORGANISM: Artificial Sequence
<220> FEATURE:
<223> OTHER INFORMATION: Synthetic construct, NPTII reverse primer

<400> SEQUENCE: 21
agccaacgta tgtcctgat                                                 19

<210> SEQ ID NO 22
<211> LENGTH: 20
<212> TYPE: DNA
<213> ORGANISM: Artificial Sequence
<220> FEATURE:
<223> OTHER INFORMATION: Synthetic construct, ODN oligonucleotide

<400> SEQUENCE: 22
tccatgacgt tcctgacgtt                                                20

<210> SEQ ID NO 23
<211> LENGTH: 11
<212> TYPE: PRT
<213> ORGANISM: Artificial Sequence
<220> FEATURE:
<223> OTHER INFORMATION: Synthetic construct, flexible linker

<400> SEQUENCE: 23

Ser Lys Ser Trp Asn Arg Ala Gln Phe Gly Ser
1               5                   10
```